(12) United States Patent
Federspiel et al.

(10) Patent No.: US 8,647,569 B1
(45) Date of Patent: Feb. 11, 2014

(54) PARACORPOREAL RESPIRATORY ASSIST LUNG

(75) Inventors: William J. Federspiel, Pittsburgh, PA (US); Brian J. Frankowski, Imperial, CA (US); Brendan C. Mack, Pasadena, CA (US); Scott W. Morley, Pittsburgh, PA (US); Meir Rosenberg, Newtown, MA (US); Robert G. Svitek, Pittsburgh, PA (US)

(73) Assignee: ALung Technologies, Inc, Pittsburgh, PA (US)

( * ) Notice: Subject to any disclaimer, the term of this patent is extended or adjusted under 35 U.S.C. 154(b) by 357 days.

(21) Appl. No.: 13/084,100

(22) Filed: Apr. 11, 2011

Related U.S. Application Data

(62) Division of application No. 11/408,650, filed on Apr. 21, 2006, now Pat. No. 7,927,544.

(60) Provisional application No. 60/688,809, filed on Jun. 8, 2005, provisional application No. 60/673,885, filed on Apr. 21, 2005.

(51) Int. Cl.
*A61M 1/00* (2006.01)
*A61M 37/00* (2006.01)
*B01D 63/00* (2006.01)
*C02F 1/44* (2006.01)

(52) U.S. Cl.
USPC ......... 422/45; 422/48; 604/6.14; 210/321.78

(58) Field of Classification Search
USPC ................. 604/4.01–6.16, 27, 122, 167; 422/44–48; 210/780–784, 231, 210/330–334, 321.78–321.81
See application file for complete search history.

(56) References Cited

U.S. PATENT DOCUMENTS 3,352,422 A  11/1967  Goran
3,422,008 A  1/1969  Mclain
(Continued)

FOREIGN PATENT DOCUMENTS

DE  10341221  3/2005
EP  057667  10/1999
(Continued)

OTHER PUBLICATIONS

Eash, Heide J. et al., "Evaluation of Fiber Bundle Rotation for Enhancing Gas Exchange in a Respiratory Assist Catheter" ASAIO Journal, Oct. 2007, pp. 368-373, vol. 53, No. 3, Lippincott, Williams and Wilkins, Philadelphia, PA.
(Continued)

*Primary Examiner* — Philip R Wiest
(74) *Attorney, Agent, or Firm* — Kathleen Kuznicki; Lynch Weis, LLC

(57) ABSTRACT

A paracorporeal respiratory assist lung is configured with an annular cylindrical hollow fiber membrane (fiber bundle) that is rotated at rapidly varying speeds. Fluid (for example, blood) is introduced to the center of the device and is passed radially through the fiber bundle. The bundle is rotated at rapidly changing velocities with a rotational actuator (for example, a motor or magnetic coupling). The rotation of the fiber bundle provides centrifugal kinetic energy to the fluid giving the device pumping capabilities and may create Taylor vortexes to increase mass transfer. Rotation of the fiber bundle increases the relative velocity between the fluid and the hollow fibers and increases the mass transfer. The porosity of the fiber bundle may be varied to enhance gas exchange with the blood. Alternatively, a rotating core may be used with a stationary fiber bundle.

5 Claims, 30 Drawing Sheets

(56) References Cited

U.S. PATENT DOCUMENTS

| | | |
|---|---|---|
| 3,841,847 A | 10/1974 | Jones et al. |
| 3,893,920 A | 7/1975 | Hubbard et al. |
| 3,934,982 A | 1/1976 | Arp |
| 3,977,976 A | 8/1976 | Spaan et al. |
| 4,033,724 A | 7/1977 | Tamiya |
| 4,038,190 A | 7/1977 | Baudet et al. |
| 4,141,835 A | 2/1979 | Schael et al. |
| 4,141,836 A | 2/1979 | Schael |
| 4,196,075 A | 4/1980 | Bentley |
| 4,201,673 A | 5/1980 | Kanno et al. |
| 4,202,776 A | 5/1980 | Joh |
| 4,212,744 A | 7/1980 | Oota |
| 4,243,532 A | 1/1981 | Tsuda et al. |
| 4,253,967 A | 3/1981 | Raible |
| 4,312,757 A | 1/1982 | Brumfield |
| 4,324,662 A | 4/1982 | Schnell |
| 4,374,802 A | 2/1983 | Fukasawa |
| 4,440,641 A | 4/1984 | Ostertag |
| 4,490,331 A | 12/1984 | Steg, Jr. |
| 4,498,990 A | 2/1985 | Shaldon et al. |
| 4,576,590 A | 3/1986 | Fiddian-green |
| 4,639,353 A | 1/1987 | Takemura et al. |
| 4,722,725 A * | 2/1988 | Sawyer et al. .................. 604/27 |
| 4,740,313 A | 4/1988 | Schoendorfer et al. |
| 4,778,445 A | 10/1988 | Hubbard et al. |
| 4,798,578 A | 1/1989 | Ranford |
| 4,911,847 A | 3/1990 | Shmidt et al. |
| 4,917,797 A | 4/1990 | Inacio et al. |
| 5,034,135 A | 7/1991 | Fischel |
| 5,034,188 A | 7/1991 | Nakanishi et al. |
| 5,039,482 A | 8/1991 | Panzani et al. |
| 5,084,011 A | 1/1992 | Grady |
| 5,102,533 A | 4/1992 | Oshiyama |
| 5,106,263 A | 4/1992 | Irie |
| 5,114,580 A | 5/1992 | Ahmad et al. |
| 5,120,502 A | 6/1992 | Gordon et al. |
| 5,152,964 A | 10/1992 | Leonard |
| 5,171,212 A | 12/1992 | Buck et al. |
| 5,188,801 A | 2/1993 | Fini |
| 5,215,519 A | 6/1993 | Shettigar |
| 5,217,689 A | 6/1993 | Raible |
| 5,225,161 A | 7/1993 | Mathewson et al. |
| 5,236,586 A | 8/1993 | Antoni et al. |
| 5,236,665 A | 8/1993 | Mathewson et al. |
| 5,240,677 A | 8/1993 | Jones et al. |
| 5,254,250 A | 10/1993 | Rolchigo et al. |
| 5,263,924 A | 11/1993 | Mathewson |
| 5,266,265 A | 11/1993 | Raible |
| 5,270,004 A | 12/1993 | Cosentino et al. |
| 5,270,005 A | 12/1993 | Raible |
| 5,290,236 A | 3/1994 | Mathewson |
| 5,338,512 A | 8/1994 | Mathewson et al. |
| 5,382,407 A | 1/1995 | Leonard |
| 5,395,525 A | 3/1995 | Takano et al. |
| 5,411,706 A | 5/1995 | Hubbard et al. |
| 5,429,802 A | 7/1995 | Hagiwara et al. |
| 5,505,842 A | 4/1996 | Enderle |
| 5,538,630 A | 7/1996 | Burns |
| 5,578,267 A | 11/1996 | Cosentino et al. |
| 5,582,794 A | 12/1996 | Hagiwara et al. |
| 5,591,404 A | 1/1997 | Mathewson |
| 5,634,892 A | 6/1997 | Whalen |
| 5,707,517 A | 1/1998 | Rolchigo et al. |
| 5,725,492 A | 3/1998 | Igo et al. |
| 5,770,149 A | 6/1998 | Raible |
| 5,817,278 A | 10/1998 | Fini et al. |
| 5,817,279 A | 10/1998 | Eilers et al. |
| 5,823,987 A * | 10/1998 | Elgas et al. .................. 604/6.13 |
| 5,830,370 A * | 11/1998 | Maloney et al. .............. 210/780 |
| 5,894,011 A | 4/1999 | Prosl et al. |
| 5,900,142 A | 5/1999 | Maloney et al. |
| 5,906,741 A | 5/1999 | Elgas et al. |
| 5,925,246 A | 7/1999 | Lee et al. |
| 5,931,802 A | 8/1999 | Yoshida et al. |
| 5,944,998 A | 8/1999 | Rolchigo et al. |
| 6,004,511 A | 12/1999 | Biscegli |
| 6,017,454 A | 1/2000 | Horl et al. |
| 6,099,730 A | 8/2000 | Ameer et al. |
| 6,106,776 A | 8/2000 | Borovetz et al. |
| 6,117,390 A | 9/2000 | Corey, Jr. |
| 6,132,613 A | 10/2000 | Hopkin et al. |
| 6,177,049 B1 | 1/2001 | Schnell et al. |
| 6,217,826 B1 | 4/2001 | Reeder et al. |
| 6,241,945 B1 | 6/2001 | Owen |
| 6,248,087 B1 | 6/2001 | Spears et al. |
| RE37,379 E | 9/2001 | Spears |
| 6,312,647 B1 | 11/2001 | Spears |
| 6,319,465 B1 | 11/2001 | Schnell et al. |
| 6,348,175 B1 | 2/2002 | Borovetz et al. |
| 6,368,557 B1 | 4/2002 | Piplani et al. |
| 6,387,323 B1 | 5/2002 | Afzal et al. |
| 6,387,324 B1 | 5/2002 | Patterson et al. |
| 6,428,747 B1 | 8/2002 | Dueri et al. |
| 6,454,999 B1 | 9/2002 | Farhangnia et al. |
| 6,503,450 B1 | 1/2003 | Afzal et al. |
| 6,565,807 B1 | 5/2003 | Patterson et al. |
| 6,596,235 B2 | 7/2003 | Divino et al. |
| 6,602,467 B1 | 8/2003 | Divino et al. |
| 6,613,279 B1 | 9/2003 | Elgas et al. |
| 6,682,698 B2 | 1/2004 | Chambers et al. |
| 6,695,807 B2 | 2/2004 | Bell et al. |
| 6,723,283 B2 | 4/2004 | Ghelli et al. |
| 6,811,750 B2 | 11/2004 | Patterson et al. |
| 6,855,291 B2 | 2/2005 | Patterson et al. |
| 6,863,821 B2 | 3/2005 | Moriarty et al. |
| 6,890,482 B2 | 5/2005 | Divino et al. |
| 6,899,847 B2 | 5/2005 | Myrick et al. |
| 6,960,322 B2 | 11/2005 | Stringer et al. |
| 6,974,435 B2 | 12/2005 | Daw et al. |
| 6,998,093 B1 | 2/2006 | Mcintosh et al. |
| 7,150,711 B2 | 12/2006 | Nüsser et al. |
| 7,172,727 B2 | 2/2007 | Patterson et al. |
| 7,238,320 B2 | 7/2007 | Ghelli et al. |
| 7,273,586 B2 | 9/2007 | Mongomery et al. |
| 7,332,125 B2 | 2/2008 | Cianci et al. |
| 7,384,543 B2 | 6/2008 | Jonsson et al. |
| 7,431,754 B2 | 10/2008 | Ogihara et al. |
| 7,455,812 B2 | 11/2008 | Thomas |
| 7,476,359 B2 | 1/2009 | Maianti et al. |
| 7,481,799 B2 | 1/2009 | Hehrlein et al. |
| 7,503,902 B2 | 3/2009 | Jensen et al. |
| 7,615,028 B2 | 11/2009 | O'mahony |
| 7,682,563 B2 | 3/2010 | Carpenter et al. |
| 7,708,942 B2 | 5/2010 | Thomas |
| 7,749,435 B2 | 7/2010 | Ogihara et al. |
| 7,927,544 B2 | 4/2011 | Federspiel et al. |
| 2005/0118059 A1 | 6/2005 | Olsen et al. |

FOREIGN PATENT DOCUMENTS

| | | |
|---|---|---|
| GB | 2092913 | 2/1982 |
| JP | 241172 | 2/1990 |
| JP | 63283709 | 11/1999 |
| WO | WO-8706151 | 10/1987 |
| WO | WO 9403266 | 2/1994 |
| WO | WO 9616684 | 6/1996 |
| WO | WO 0038817 | 7/2000 |
| WO | WO 2006031858 | 3/2006 |
| WO | WO 2006066553 | 6/2006 |

OTHER PUBLICATIONS

Snyder, Trevor A et al., Blood Biocompatibility Assessment of an Intraveneous Gas Exchange Device, Artificial Organs, Sep. 2006, pp. 657-665, vol. 30 No. 9, Blackwell Science, Inc. Boston, MA.

Eash, Heide J. et al., "Evaluation of Plasma Resistant Hollow Fiber Membranes for Artificial Lungs," ASAIO Journal, Oct. 2004, pp. 491-497, vol. 50, No. 5, Lippincott, Williams and Wilkins, Philadelphia, PA.

Federspiel, William J. et al., "Ex Vivo Testing of the Intravenous Membrane Oxygenator," ASAIO Journal, May-Jun. 2000, pp. 261-267, vol. 46, No. 3, Lippincott, Williams and Wilkins, Philadelphia, PA.

(56) References Cited

OTHER PUBLICATIONS

Federspiel, William J. et al., "Experimental Evaluation of a Model for Oxygen Exchange in a Pulsating Intravascular Artificial Lung," Annals of Biomedical Engineering, Feb. 2000, pp. 160-167, vol. 28, No. 2, Springer Science+Business Media, New York, NY.

Federspiel, William J. et al., "Lung, Artificial: Basic Principles and Current Applications," Encyclopedia of Biomaterials and Biomedical Engineering, 1st Edition, Jul. 2004, pp. 810-921, Informa Healthcare, London, UK.

Federspiel, William J. et al., "Lung, Artificial: Current Research and Future Directions," Encyclopedia of Biomaterials and Biomedical Engineering, 1st Edition, Jul. 2004, pp. 922-931, Informa Healthcare, London, UK.

Hattler, Brack G., et al., "A Respiratory Gas Exchange Catheter: In Vitro and In Vivo Tests in Large Animals," The Journal of Thoracic and Cardiovascular Surgery, Sep. 2002, pp. 520-530, vol. 124, Elsevier, Amsterdam, Netherlands.

Hattler, Brack G., et al., "The Artificial Lung," Lung Transplantation, Jun. 2003, pp. 386-398, Cambridge University Press, Cambridge, UK.

Hout, Mariah S. et al., "Mathematical and Experimental Analyses of Antibody Transport in Hollow-Fiber-Based Specific Antibody Filters," Biotechnology Progress, Sep.-Oct. 2003, pp. 1553-1561, ACS Publications, Washington, DC.

Hout, Mariah S. et al., "Validation of a Model for Flow-Dependent Carbon Dioxide Exchange in Artificial Lungs," Artificial Organs, Feb. 2010, pp. 114-118, vol. 24, No. 2, Blackwell Science, Inc., Boston, MA.

Kaar, Joel L. et al., "Towards Improved Artificial Lungs Through Biocatalysis," Biomaterials, Jul. 2007, pp. 3131-3139, vol. 28, No. 20, Elsevier, Amsterdam, Netherlands.

Kono, Satoshi et al., "Autosynchronized Systolic Unloading During Left Ventricular Assist with a Centrifugal Pump," The Journal of Thoracic and Cardiovascular Surgery, Feb. 2003, pp. 353-360, vol. 125, Elsevier, Amsterdam, Netherlands.

Lund, Laura W. et al., "A Comparative In Vitro Hemolysis Study of a Pulsating Intravenous Artificial Lung" ASAIO Journal, Nov.-Dec. 2002, pp. 631-635, vol. 48, No. 6, Lippincott, Williams and Wilkins, Philadelphia, PA.

Nosé, Yukihiko et al., "Development of a Totally Implantable Biventricular Bypass Centrifugal Blood Pump System," The Annals of Thoracic Surgery, Aug. 1998, pp. 775-779, vol. 68, No. 2, Elsevier, Amsterdam, Netherlands.

Svitek, R.G. et al., "Evaluation of a Pumping Assist Lung That Uses a Rotating, Fiber Bundle," ASAIO Journal, Nov.-Dec. 2005, pp. 773-780, vol. 51, No. 6, Lippincott, Williams and Wilkins, Philadelphia, PA.

Svitek, R.G., "Development of a Paracorporeal Respiratory Assist Lung," Jun. 2006, University of Pittsburgh, Pittsburgh, PA.

Berryessa, Richard et al., "A Technique for the Effective Removal of Air from a Hollow Fiber Membrane Oxygenator Circuit," The Journal of Extracorporeal Technology, 1986, pp. 156-158, vol. 18, American Society of Extra-Corporeal Technology, Inc., Richmond, VA.

Bodell, Bruce R. et al., "An Implantable Artificial Lung," Journal of the American Medical Association, Jan. 25, 1965, pp. 125-127, vol. 191, No. 4, American Medical Association, Chicago, IL.

Cattaneo, Giorgio et al., "Compact Intra- and Extracorporeal Oxygenator Developments," Perfusion, May 2004, 251-255, vol. 19, No. 3, Sage Publications, Thousand Oaks, CA.

Conrad, Steven A., et al., "Total Extracorporeal Arteriovenous Carbon Dioxide Removal in Acute Respiratory Failure: A Phase I Clinical Study," Intensive Care Medicine, Jun. 15, 2001, vol. 27, Springer Science+Business Media, New York, NY.

Federspiel, William J. et al., "Development of a Low Flow Resistance Intravenous Oxygenator," ASAIO Journal, Sep.-Oct. 1997, pp. M725-M730, vol. 43, No. 5, Lippincott, Williams and Wilkins, Philadelphia, PA.

Federspiel, William J. et al., "Gas Flow Dynamics in Hollow-Fiber Membranes," AIChE Journal, Jul. 1996, pp. 2094-2099, vol. 42, No. 7, American Institute of Chemical Engineers, John Wiley & Sons Inc., Malden, MA.

Federspiel, William J. et al., "Recent Progress in Engineering the Pittsburgh Intravenous Membrane Oxygenator," ASAIO Journal, Sep.-Oct 1996, pp. M435-M442, vol. 42, No. 5, Lippincott, Williams and Wilkins, Philadelphia, PA.

Federspiel, William J. et al., "Sweep Gas Flowrate and CO2 Exchange in Artificial Lungs," Artificial Organs, Sep. 1996, pp. 1050-1056, vol. 20, No. 9, Blackwell Science, Inc., Boston, MA.

Federspiel, William J. et al., "Temporary Support of the Lungs—the Artificial Lung," The Transplantation and Replacement of Thoracic Organs, Second Edition, Oct. 1996, pp. 717-728, Kluwer Academic Publishers, Lancaster, United Kingdom.

Golob, Joseph F., et al., "Acute In-Vivo Testing of an Intravascular Oxygenator," ASAIO Journal, Sep.-Oct. 2001, pp. 432-437, vol. 47, No. 5, Lippincott, Williams and Wilkins, Philadelphia, PA.

Hattler, Brack G., et al., "Development of an Intravenous Membrane Oxygenator: Enhanced Intravenous Gas Exchange Through Convective Mixing of Blood around Hollow Fiber Membranes," Artificial Organs, Nov. 1994, pp. 806-812, vol. 18, No. 11, Blackwell Science, Inc., Boston, MA.

Hattler, Brack G., et al., "Gas Exchange in the Venous System: Support for the Failing Lung" The Artificial Lung, Jan. 2002, pp. 132-174, Landes Bioscience, Austin, TX.

Hattler, Brack G., et al., "Progress With the Development of the Intravenous Membrane Oxygenator," Perfusion, Jul. 1, 1999, 311-315, vol. 14, No. 4, Sage Publications, Thousand Oaks, CA.

Hattler, Brack G., et al., "Respiratory Dialysis, A New Coricept in Pulmonary Support" ASAIO Journal, Jul.-Sep. 1992, pp. M322-M325, vol. 38, No. 3, Lippincott, Williams and Wilkins, Philadelphia, PA.

Henchir, Kristie A. et al., "Development of Microfabricated Biohybrid Artificial Lungs," Powerpoint slides for presentation at the 51st annual meeting of the American Society for Artificial Internal Organs (ASAIO), Jun. 2005, Washington, DC.

Henchir, Kristie A. et al., "Toward Biohybrid Artificial Alveolar—Capillary (AAC) Modules for Artificial Lung Applications," Powerpoint slides for presentation at the 51st annual meeting of the American Society for Artificial Internal Organs (ASAIO), Jun. 2005, Washington, DC.

Hewitt, Todd J. et al., "A Mathematical Model of Gas Exchange in an Intravenous Membrane Oxygenator," Annals of Biomedical Engineering, Jan. 1998, pp. 166-178, vol. 26, No. 1, Springer Science+Business Media, New York, NY.

Hung, Tin-Kan et al., "Intravenous Membrane Oxygenators With Balloon Pumping," Biomechanics: Proceedings of The Fourth China-Japan-USA-Singapore Conference on Biomechanics, May 1995, pp. 381-384, World Scientific Publishing Company, Inc., Singapore.

Jegaden, Olivier et al., Letter to the Editor, "Temporary Left Ventricular Assistance With a Hemopump Assist Device During Acute Myocardial Infarction," The Journal of Thoracic and Cardiovascular Surgery, Aug. 1990, pp. 228-232, vol. 100, Elsevier, Amsterdam, Netherlands.

Kolobow, Theodore et al., "Construction and Evaluation of an Aveolar Membrane Artifical Heart-Lung," ASAIO Journal, Apr. 1963, pp. 238-243, vol. 9, Lippincott, Williams and Wilkins, Philadelphia, PA.

Konishi, Ruriko et al., "Nitric Oxide Prevents Human Platelet Adhesion to Fiber Membranes in Whole Blood,"ASAIO Journal, Sep.-Oct. 1996, pp. M850-M853, vol. 42, No. 5, Lippincott, Williams and Wilkins, Philadelphia, PA.

Lund, Laura W. et al., "A Novel Method for Measuring Hollow Fiber Membrane Permeability in a Gas-Liquid System," ASAIO Journal, Sep.-Oct. 1996, pp. M446-M451, vol. 42, No. 5, Lippincott, Williams and Wilkins, Philadelphia, PA.

Lund, Laura W. et al., "Gas Permeability of Hollow Fiber Membranes in a Gas-Liquid System," Journal of Membrane Science, 1996, pp. 207-219, No. 117, Elsevier, Amsterdam, Netherlands.

(56) References Cited

OTHER PUBLICATIONS

Lund, Laura W. et al., "Is Condensation the Cause of Plasma Leakage in Microporous Hollow Fiber Membrane Oxygenators," Journal of Membrane Science, 1998, pp. 87-93, No. 147, Elsevier, Amsterdam, Netherlands.

Lund, Laura W., online brochure, "Hollow Fiber Membrane Permeability Analysis," UPMC Artificial Lung Laboratory: Ongoing Projects 2, Jun. 15, 2001, web page http://www.pitt.edu/wfedersp/Brochure/Projects2.html, University of Pittsburgh Medical Center, Pittsburgh, PA.

Macha, Mahender et al., "Acute in Vivo Studies of the Pittsburgh Intravenous Membrane Oxygenator," ASAIO Journal, Sep.-Oct. 1996, pp. M609-M615, vol. 42, No. 5, Lippincott, Williams and Wilkins, Philadelphia, PA.

Marcolin, R. et al., "Ventilatory Impact of Partial Extracorporeal CO2 Removal (PECOR) in ARF Patients," ASAIO Transactions, Jul.-Sep. 1986, pp. 508-510, vol. 32, No. 1, American Society for Artificial Internal Organs, Boca Raton, FL.

Miller, Gerald E. et al., "A Multiple Disk Centrifugal Pump as a Blood Flow Device," IEEE Transactions on Biomedical Engineering, Feb. 1990, pp. 157-163, vol. 37, No. 2, IEEE Engineering in Medicine and Biology Society, Gainesville, FL.

Miller, Gerald E. et al., "Analysis of Optimal Design Configurations for a Multiple Disk Centrifugal Blood Pump," Artificial Organs, Jun. 1999, pp. 559-565, vol. 23, No. 6, Blackwell Science, Inc., Boston, MA.

Mockros, L.F. et al., "Compact Cross-Flow Tubular Oxygenators," ASAIO Journal, Apr. 1985, pp. 628-633, vol. 41, No. 1, Lippincott, Williams and Wilkins, Philadelphia, PA.

Mortensen, J.D. et al., "Conceptual and Design Features of a Practical, Clinically Effective Intravenous Mechanical Blood Oxygen/Carbon Dioxide Exchange Device (Ivox)," The International Journal of Artificial Organs, Jun. 1989, pp. 384-389, vol. 12, No. 6, Wichtig Editore, Naples, Italy.

Mortensen, J.D., "An Intravenacaval Blood Gas Exchange (IVCBGE) Device: A Preliminary Report," ASAIO Transactions, Jul.-Sep. 1987, pp. 570-573, vol. 33, No. 3, American Society for Artificial Internal Organs, Boca Raton, FL.

Reeder, Gary D. et al., "Current Progress in the Development of an Intravenous Membrane Oxygenator," ASAIO Journal, Jul.-Sep. 1993, pp. M461-M465, vol. 39, No. 3, Lippincott, Williams and Wilkins, Philadelphia, PA.

Riley, Jeffrey B. et al., "Blood Oxygenation Control by Vacuum Drawn Mixture of Room Air and Oxygen in a Membrane Oxygenator," The Journal of Extracorporeal Technology, 1980, pp. 46-46, vol. 12, No. 2, American Society of Extra-Corporeal Technology, Inc. Richmond, VA.

Ross, Ian M. et al., "Carbon Dioxide Flush and Vacuum Priming of the Travenol Membrane Oxygenator," Proceedings of the American Academy of Cardiovascular Perfusion, Jan. 1982, pp. 58-59, vol. 3, American Academy of Cardiovascular Perfusion, Annville, PA.

Shah, Ashish H. et al., "Vibration Analysis of Vessel Wall Motion with Intra Vena Caval Balloon Pumping," ASAIO Journal, Jul.-Sep. 1994, pp. M740-M742, vol. 40, No. 3, Lippincott, Williams and Wilkins, Philadelphia, PA.

Shiya, Norihiko et al., "Effects of Hemopump Support on Left Ventricular Unloading and Coronary Blood Flow," ASAIO Journal, Jul.-Sep. 1991, pp. M361-M362, vol. 37, No. 3, Lippincott, Williams and Wilkins, Philadelphia, PA.

Tanashita, K. et al., "Augmentation of Gas Transfer with Pulsative Flow in the Coiled Tube Membrane Oxygenator Design," ASAIO Journal, 1980, pp. 561-566, vol. 26, Lippincott, Williams and Wilkins, Philadelphia, PA.

Vaslef, Steven D. et al., "Development of an Intravascular Lung Assist Device," ASAIO Transactions, Jul.-Sep. 1989, pp. 660-664, vol. 35, No. 3, American Society for Artificial Internal Organs, Boca Raton, FL.

Zwischenberger, Joseph B. et al., "Percutaneous Extracorporeal Arteriovenous CO2 Removal for Severe Respiratory Failure," Annals of Thoracic Surgery Jan. 1999, pp. 181-182, vol. 68, No. 1, Elsevier, Amsterdam, Netherlands.

Zwischenberger, Joseph B. et al., "The Paracorporeal Artifical Lung Improves 5-Day Outcomes form Lethal Smoke/Burn-Induced Acute Respiratory Distress Syndrome in Sheep," Annals of Thoracic Surgery, Oct. 2002, pp. 1017-1018, vol. 74, No. 4, Elsevier, Amsterdam, Netherlands.

\* cited by examiner

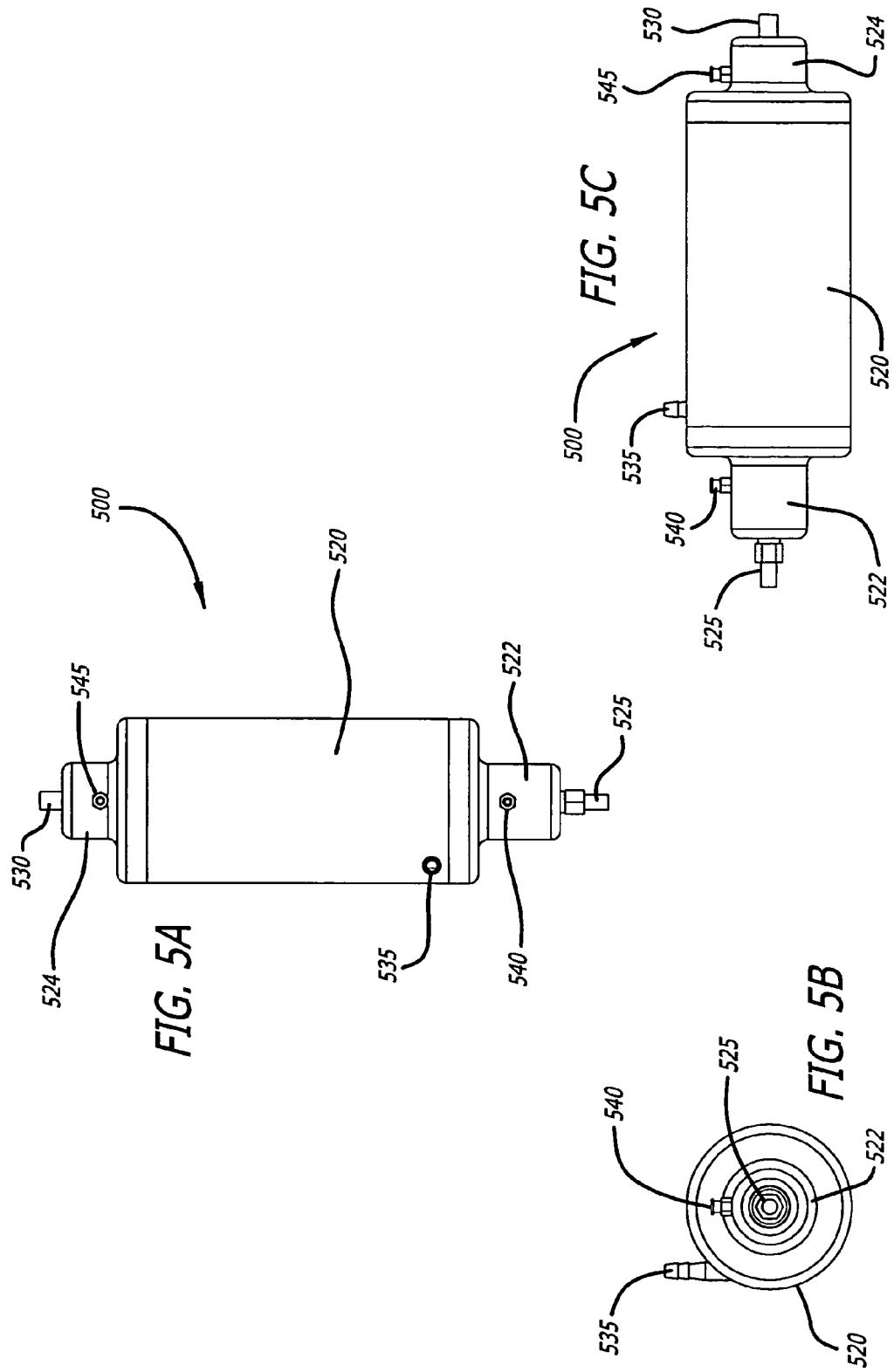

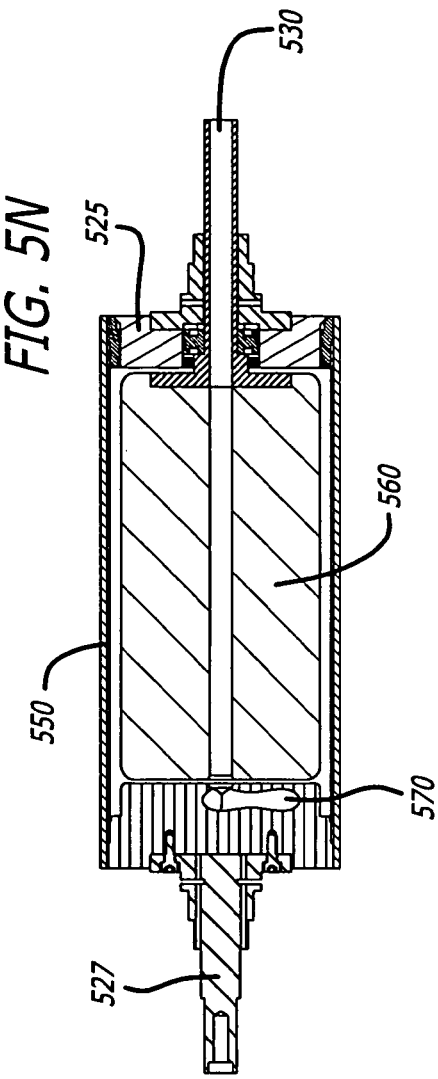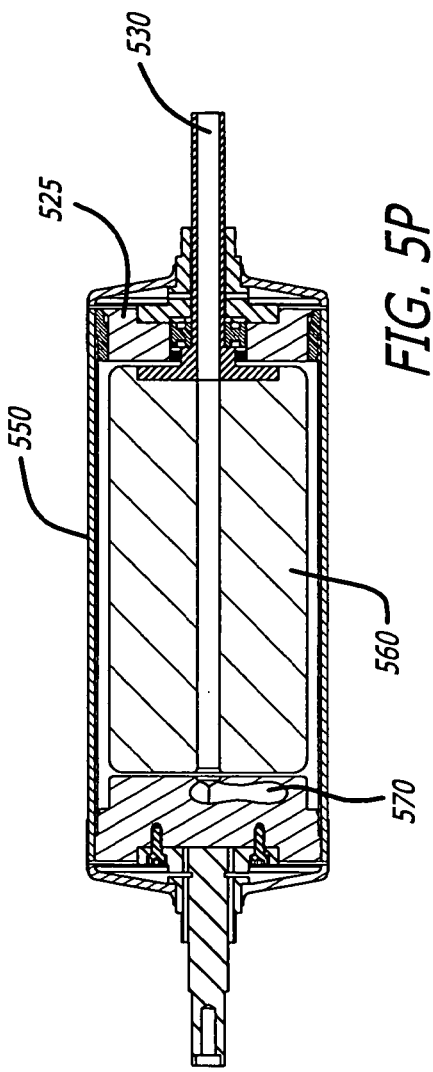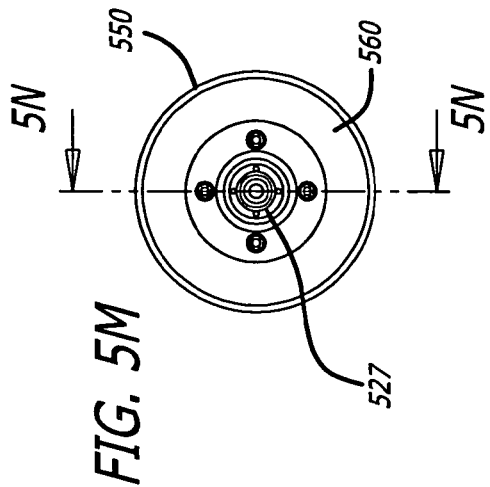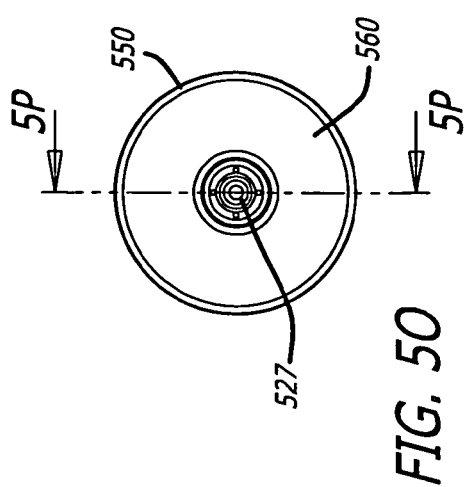

PARACORPOREAL RESPIRATORY ASSIST LUNG

CROSS-REFERENCES TO RELATED APPLICATIONS

This is a divisional application which is based on U.S. Ser. No. 11/408,650, filed on Apr. 21, 2006, U.S. Pat. No. 7,927,544 with an issue date of Apr. 19, 2011; which claims priority from U.S. Provisional Patent Application Ser. No. 60/673,885, filed Apr. 21, 2005 and U.S. Provisional Patent Application Ser. No. 60/688,809, filed Jun. 8, 2005, each of which are incorporated by reference in their entirety.

FEDERALLY SPONSORED RESEARCH

The U.S. Government has a paid-up license in this invention and the right in limited circumstances to require the patent owner to license others on reasonable terms as provided for by the terms of Grant Nos. DAMD 17-02-1-0717 awarded by the Department of the Army and Grant No. RO1 HL 70051 awarded by the National Institutes of Health.

BACKGROUND OF THE INVENTION

The present invention is directed to an improved veno-venous extracorporeal oxygenator, referred to herein as a "paracorporeal respiratory assist lung" or the "PRAL device." More specifically, the paracorporeal respiratory assist lung includes a variable speed (oscillating) rotating fiber bundle having increased porosity. In addition, the PRAL device may be configured to rotate a core wherein the fiber bundle is stationary, and may further be configured to include a fiber bundle on the rotating core.

It has been reported that 350,000 Americans die of lung disease each year, most from Acute Respiratory Distress Syndrome (ARDS) and Chronic Obstructive Pulmonary Disease (COPD). The most common treatment is mechanical ventilation, but may further exacerbate respiratory insufficiency and can cause serious side effects, such as barotrauma and volutrauma. It has been further reported that heart-lung machines, which utilize oxygenators, are employed during surgery throughout the world hundreds of thousands of times per year. Such oxygenators may be useful in treating COPD and ARDS. However, inefficient mass transfer (gas exchange) of oxygen and carbon dioxide is a common problem in oxygenators used in heart-lung machines.

The use of membrane oxygenators to oxygenate blood is well known in the art. One type of conventional membrane oxygenator employs bundles of hollow fibers retained within a cylindrical housing wherein oxygen is pumped through the hollow fibers in the same direction as the blood. The hollow fibers consist of a microporous membrane which is impermeable to blood and permeable to gas. Gas exchange takes place when venous blood flows through the housing and contacts the hollow fibers. Based on the law of diffusion, the oxygen diffuses across the hollow fiber walls and enriches venous blood in contact with these hollow fibers. A stated disadvantage to this type of membrane oxygenator is that a blood boundary layer is formed around the hollow fibers which retards oxygenation of blood that does not directly contact the hollow fibers.

Another known type of membrane oxygenator includes moving a portion of the oxygenator to provide increased mixing of blood flow. In this type of membrane oxygenator, a blood flow path and an oxygen flow path are positioned between a rotor and a stator and separated by a membrane and a wafer. When the rotor rotates relative to the stator, mixing of blood flow occurs resulting in disruption of the blood boundary layer. Although such an oxygenator provides a degree of mixing of blood, this mixing may cause destruction of red blood cells. In one embodiment of such an oxygenator, a cylindrical, semi-permeable membrane containing oxygen is rotated in a housing such that blood contacts and flows over the membrane and oxygen is transferred through the rotating membrane to the blood. One reported problem with this type of membrane oxygenator is the poor permeability to oxygen and carbon dioxide of semi-permeable membranes.

Yet another known membrane oxygenator includes hollow fiber membranes that extend substantially longitudinally, first inert fibers are spaced between them and also extend substantially longitudinally. Second inert fibers extend generally transverse to the hollow fibers and generally contiguous therewith, so that an oxygen-containing gas can pass through the hollow fibers and blood can be passed over their exterior for gas exchange through the membrane. The second inert fibers may form a weft and the first inert fibers are spaced one between each two hollow fibers so that the warp consists of alternating strands of hollow fiber and first inert fiber passing over the weft in an oscillating fashion. The inert fibers are disclosed as biocompatible monofilament polymers that provide spacing of the hollow fibers to produce even blood films. However, such an oxygenator is not designed for extracorporeal applications having relatively low blood flow rates.

Accordingly, there is a need for, and what was heretofore unavailable, an extracorporeal oxygenator having enhanced gas exchange characteristics resulting from a variable rotating fiber bundle and/or increased porosity of the fiber bundle that has high gas exchange efficiency with minimal damage to the blood components.

SUMMARY OF THE INVENTION

The present invention is directed to an improved veno-venous extracorporeal oxygenator, referred to herein as a "paracorporeal respiratory assist lung." The veno-venous artificial lung may be used as replacement therapy for mechanical ventilation for chronic obstructive pulmonary disease (COPD) patients with high levels of partial pressure of carbon dioxide ($pCO_2$) in their blood. The paracorporeal respiratory assist lung of the present invention provides active mixing through rotation of a module containing gas-permeable, hollow fibers (annular fiber bundle) for enhanced gas exchange at constant flow rates of blood through the device. Rotation of the fiber bundle is known to increase the gas exchange efficiency of artificial lungs, for example, a two-hundred percent increase in carbon dioxide ($CO_2$) transfer efficiency. It has been demonstrated that $CO_2$ removal of 100-120 milliliters per minute (ml/min) can be achieved with blood flow rates in the range of 0.5 to 1.0 liters per minute (l/min). The rotating fiber bundle provides self-pumping of blood through the device with pressure heads below thirty millimeters of mercury (mmHg). It has been demonstrated that self-pumping of blood through the device with pressure heads that can be tailored to the application by altering the diameter of the annular fiber bundle or the speed of rotation. Prototypes with fiber bundle diameters up to 4 inches size have generated pressure heads up to 100-300 mmHg. Accordingly, the paracorporeal respiratory assist lung acts as an integrated pump/hollow fiber membrane mass transport device.

One aspect of the improvements to the paracorporeal respiratory assist lung according to the present invention includes an annular cylindrical hollow fiber membrane device that is rotated at rapidly varying speeds. Fluid is introduced to the center of the device and is passed radially through the fiber bundle. The bundle is rotated at rapidly changing velocities with a rotational actuator (usually a motor). It has been demonstrated that the present invention enhances mass transfer when the rotational velocity of the fiber bundle is rapidly varied. For example, oscillations are introduced in the steady rotation of a hollow fiber bundle to increase the mass transfer efficiency of the device while maintaining its pumping capabilities.

Another aspect of the improvements to the paracorporeal respiratory assist lung according to the present invention includes increasing the porosity in the rotating fiber bundle. The increased porosity provides more fluid to flow through the fiber bundle, thus increasing the overall mass transfer efficiency of the device. The extra porosity in the fiber bundle is created by several possible ways including, but not limited to, using spacers to create void space between the fiber layers, removing every other fiber in the mat and using smaller diameter fibers. Additionally, support threads could be removed from the fiber fabric, and the paracorporeal respiratory assist lung could be configured such that the manifolds are relatively closer so as to "puff out" the fiber bundle.

A further aspect of the present invention includes a paracorporeal respiratory assist lung having the following features:
  Paracorporeal veno-venous system with percutaneous cannula
  Inserted in the venous circulation for blood flow
  Self-pumping of blood flow driven by rotating fiber bundle
  Removes $CO_2$ and supplies $O_2$ before blood reaches the lungs
  Gas exchange at blood flow rates of less than one liter per minute
  Rotating hollow fiber bundle for enhanced gas exchange
  Rotating annular fiber bundle promotes increased flow velocity past fiber surfaces
  Stationary core and outer housing generate fluid shear on fiber bundle
  Blood pathway allows rotating bundle to pump fluid
  Compact, efficient hollow fiber module worn externally
  Additional features of the paracorporeal respiratory assist lung of the present invention include:
  Variable rotation enhances gas exchange
  Variable porosity of the fiber bundle
  Blood flows of 500-750 ml/min for respiratory support
  Small dual-lumen cannula (14-16 French)
  Active surface area of the fiber bundle is less than 0.50 square meters ($m^2$)
  $CO_2$ removal of 100-120 ml/min at blood flow rate of 0.5 to 1.0 liters per minute
  $CO_2$ removal independent of the functional capacity of the natural lungs One embodiment of the present invention includes a paracorporeal respiratory assist lung having a housing having a liquid inlet, a liquid outlet, a gas inlet and a gas outlet. The PRAL device includes a plurality of tubular gas permeable fiber membranes configured to form a fiber bundle, the fiber bundle being disposed within the housing and connected to and in fluid communication with the gas inlet and the gas outlet, wherein a first gap is configured between the housing and the fiber bundle. The device further includes a stationary core being disposed within the fiber bundle, wherein a second gap is configured between the core and the fiber bundle. The PRAL device may be configured for rotating the fiber bundle, wherein the housing, fiber bundle and core are configured such that liquid entering the liquid inlet passes through the fiber bundle and into the liquid outlet.

An alternative embodiment of the paracorporeal respiratory assist lung of the present invention includes a housing having a liquid inlet, a liquid outlet, a gas inlet and a gas outlet. The PRAL device includes a plurality of tubular gas permeable fiber membranes configured to form a fiber bundle, the fiber bundle being disposed within the housing and connected to and in fluid communication with the gas inlet and the gas outlet, wherein a first gap is configured between the housing and the fiber bundle. The device is configured with a core being disposed within the fiber bundle, wherein a second gap is configured between the core and the fiber bundle. The device may include a mechanism for rotating the core, wherein the housing, fiber bundle and core are configured such that liquid entering the liquid inlet passes through the fiber bundle and into the liquid outlet. The PRAL device may further be configured for creating turbulent flow within the second gap and creating a plurality of Taylor vortexes within the second gap. In addition, the fiber bundle may be configured with a porosity that allows uniform liquid flow though the fiber bundle. Further, the PRAL device may be configured such that the first gap and the second gap are configured to optimize liquid flow through the fiber bundle.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

Figure 1:
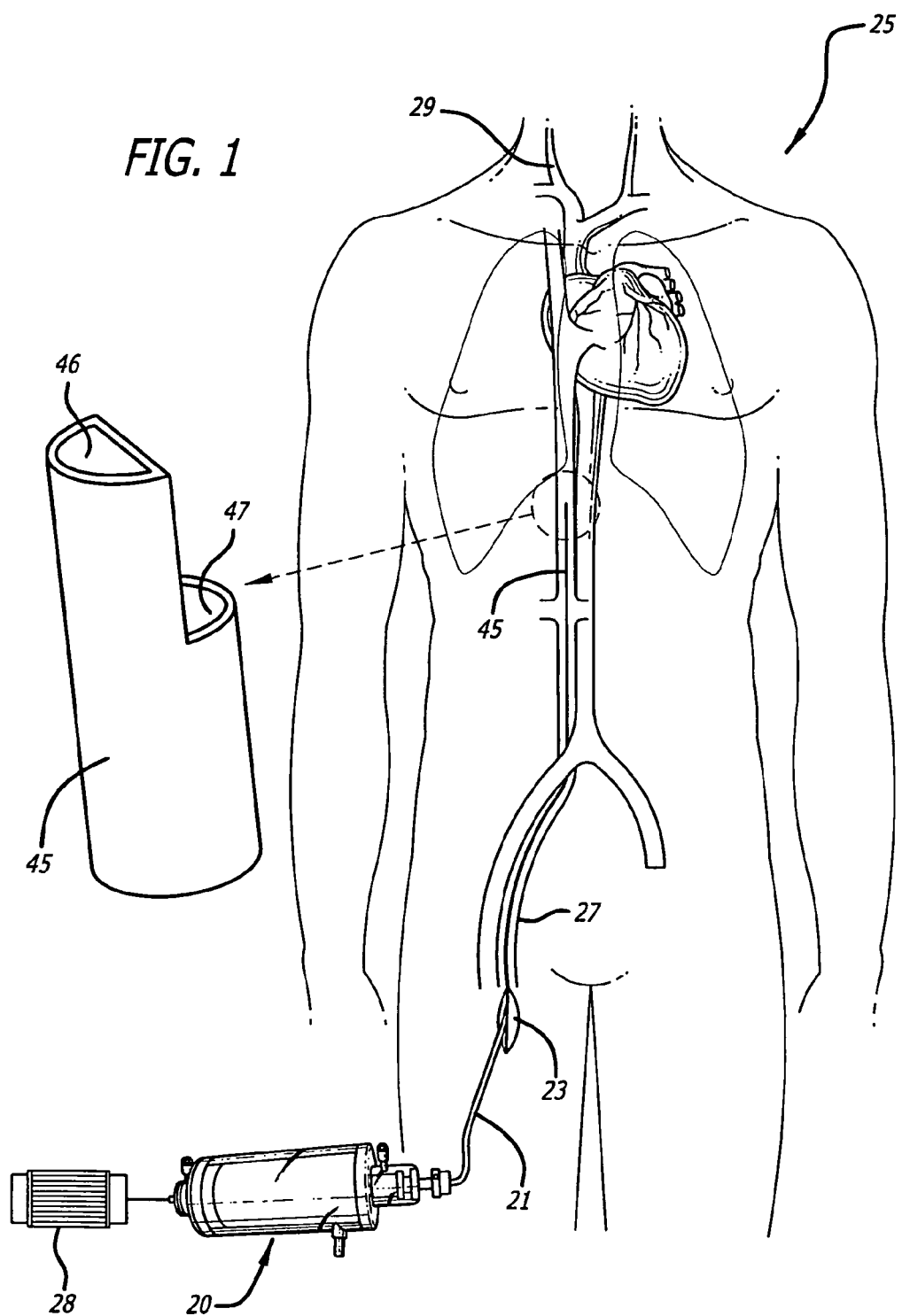
FIG. 1 depicts placement in vivo of the paracorporeal respiratory assist lung of the present invention.

The present invention is directed to an improved veno-venous extracorporeal oxygenator, referred to herein as a "paracorporeal respiratory assist lung" or "PRAL device." The paracorporeal respiratory assist lung of the present invention includes a rotating hollow fiber membrane bundle to increase the gas exchange efficiency of the device by reducing the boundary layer phenomena caused by blood flowing over the fibers. U.S. Pat. Nos. 5,830,370 (Maloney et al.); 5,900,142 (Maloney et al.); 6,106,776 (Borovetz et al.); 6,217,826 (Reeder et al.); 6,348,175 (Borovetz et al.); 6,723,284 (Reeder et al.) and U.S. Publication No. 2004/0219,061 (Reeder et al.) are incorporated herein in their entirety by reference.

The paracorporeal respiratory assist lung of the present invention has been developed for patients suffering from acute lung failures and acute exacerbations of chronic lung diseases. The design concept builds upon the clinical success of previous oxygenators that remove blood from the femoral artery of the patient, removes carbon dioxide ($CO_2$) via a commercially available membrane oxygenator and utilizes the natural arterio-venous pressure gradient to direct the blood to the femoral vein. The present invention uses an annular rotating hollow fiber membrane bundle to increase gas exchange and enable the device to pump blood. The increased gas exchange enables a lower surface area than current commercially available membrane lungs, and the pumping capacity of the rotating bundle enables blood flow through a percutaneous dual lumen cannula inserted exclusively on the venous circulation.

The main limitation to gas transfer in blood oxygenators is the diffusional boundary layer created by fluid flow along the surfaces of the fiber membranes. Effective movement of the fibers relative to the fluid (blood) can help reduce this boundary layer. In the invention described here, the hollow fibers of the oxygenator are configured into an annular bundle that is rotated about a central axis. The placement of the hollow fibers in an annulus distinguishes this rotating oxygenator from known spinning disk rotating oxygenators. In such an annular configuration, the spinning of the fiber bundle provides a more uniform linear velocity to the fibers because all the fibers are at comparable distance from the axis of rotation. Accordingly, the paracorporeal respiratory assist lung of the present invention can achieve a given level of gas exchange at lower rotational speed than in spinning disk type oxygenators.

The paracorporeal respiratory assist lung of the present invention includes an outer housing that incases the fiber annulus, a motor connected to a shaft that spins the fiber annulus, and seals and bearings that separate the fluid and gas pathways. The proximal and distal manifolds may be configured with mechanisms, such as vanes, to aid in the mixing of fresh blood into the spinning fiber bundle. The fluid (blood/water) flows through a center pathway within the rotating shaft of the device that supports the fibers. With the rotation of this fluid pathway/fiber assembly, the fluid velocities that pass through the fibers and exchange gas can be regulated by controlling the rotational rate of the fiber bundle. With the fiber annulus of this device configured to a set distance from the center of rotation, more consistent velocities past the fibers are achieved, uniformly utilizing all the fibers, unlike a disc type oxygenator that generates various velocities along their surfaces.

The paracorporeal respiratory assist lung of the present invention has distinct advantages over current rotational technologies:
- rotating annular fiber bundle instead of a stationary fiber bundle;
- rotating fiber bundle in annular shape instead of disk (velocity does not go to zero near the axis of rotation);
- rotation can be steady/unsteady (time varying increases mass transfer and pumping at the mean steady value);
- annulus can be fabricated over a range of porosities (higher porosity leads to higher gas exchange without a significant effect on pumping);
- the annulus can be a thin bundle which leads to more shear penetration from the stationary walls surrounding the bundle;
- hemolysis is not due to the rotating fibers themselves (the device is configured using a porous stainless steel cage for support during rotation);
- various technologies have been developed to vary the fiber bundle porosity;
- rotation of the fiber bundle appears to make the flow paths more uniform so that gas exchange is not affected by the design or location of the inflow/outflow ports;
- pumping allows veno-venous percutaneous operation; and levels of $CO_2$ removal due to rotation of the fiber bundle may enable respiratory dialysis or low-flow $CO_2$ removal.

As shown in FIG. 1, a paracorporeal respiratory assist lung (PRAL device) is configured with a motor drive 28 for positioning outside of the body of a patient 25. The PRAL device includes a blood flow catheter 21 that may be inserted into the femoral vein 27 of the patient. Alternatively, the PRAL blood catheter may be inserted through the jugular vein 29 of the patient. The proximal end 45 of the PRAL blood catheter 21 may be inserted through a cut down 23 or percutaneous access in the leg of the patient for placement into the femoral vein. The catheter is guided through the patient's vasculature to a position proximate the patient's heart such that the distal end 45 is close to the heart, for example in or near the vena cava. The PRAL blood catheter may be configured with a dual lumen having one side 47 for a blood inlet and a second side 46 for a blood outlet. It may be advantageous to notch the catheter distal end such that the blood outlet end 46 extends distal of the blood inlet opening 47.

Figure 2A:
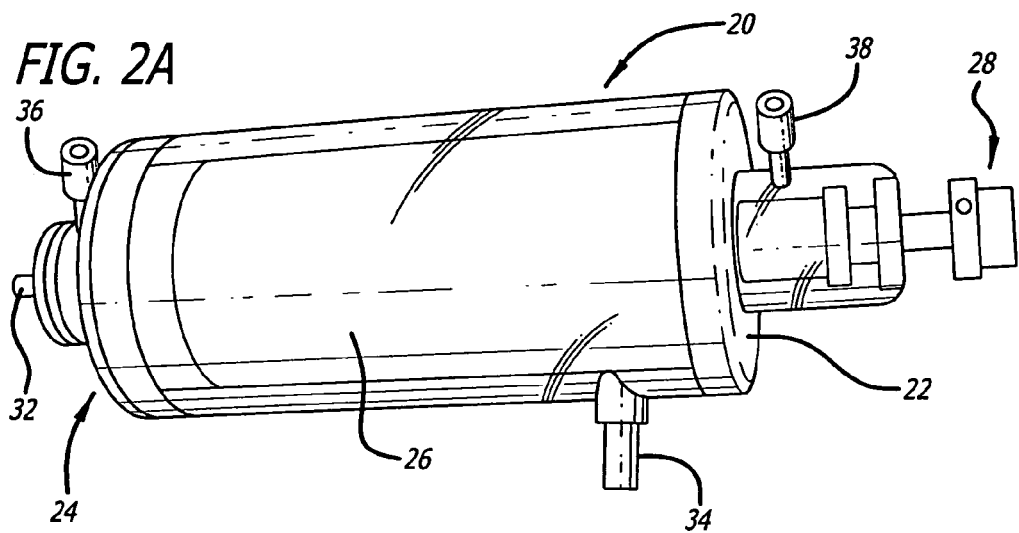
FIGS. 2A-2C depict several views of one embodiment of the paracorporeal respiratory assist lung of the present invention.
Figure 2B:
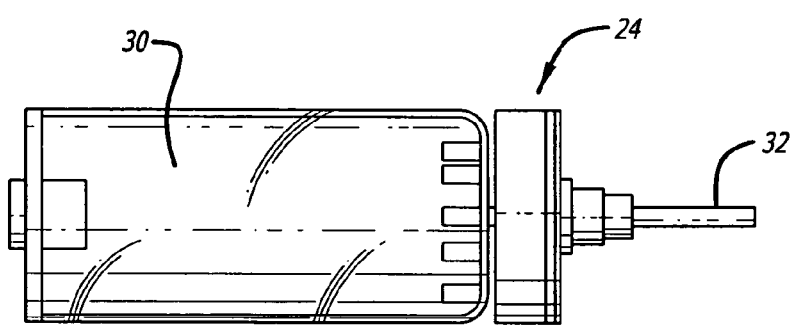
Figure 2C:
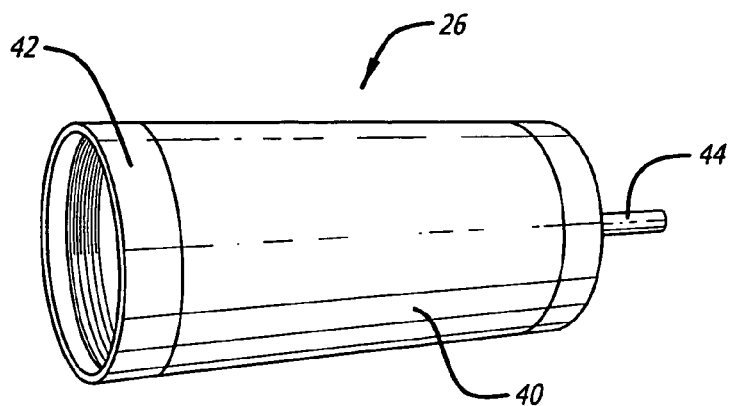
Figure 3A:
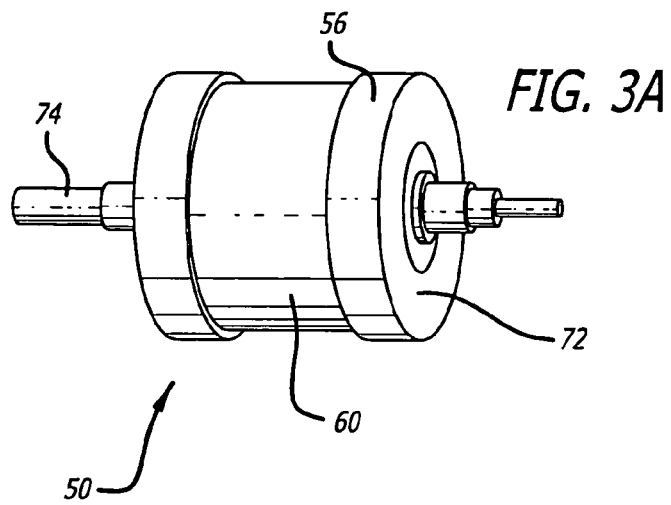
FIGS. 3A-3D depict several views of an alternative embodiment of the paracorporeal respiratory assist lung of the present invention.
Figure 3B:
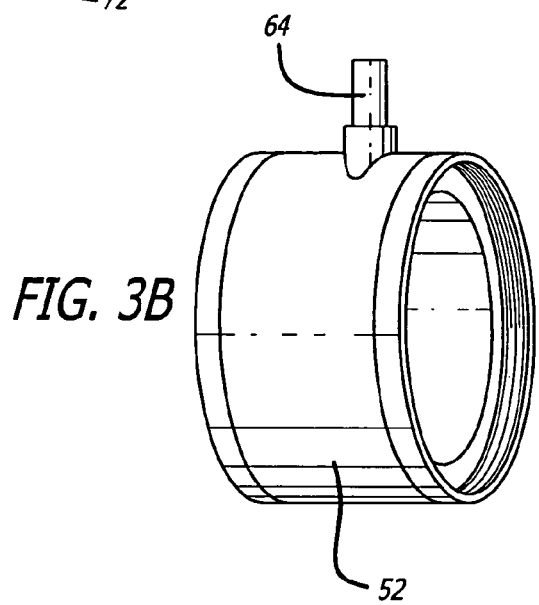
Figure 3C:
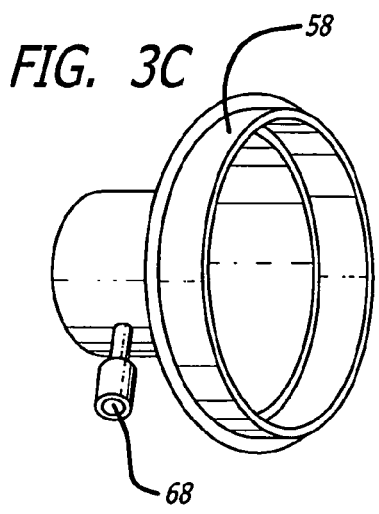
Figure 3D:
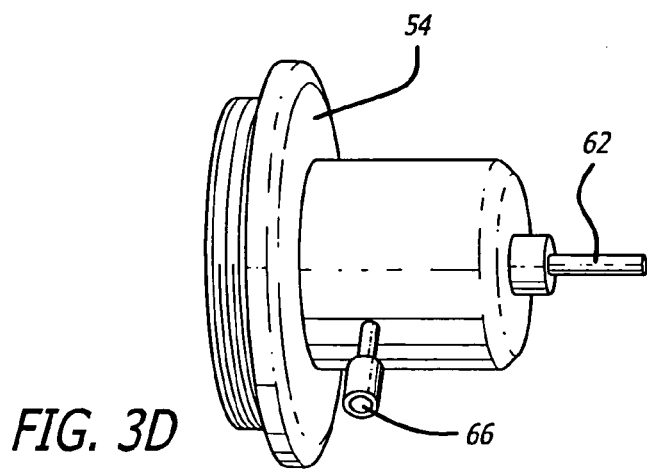
Figure 16A:
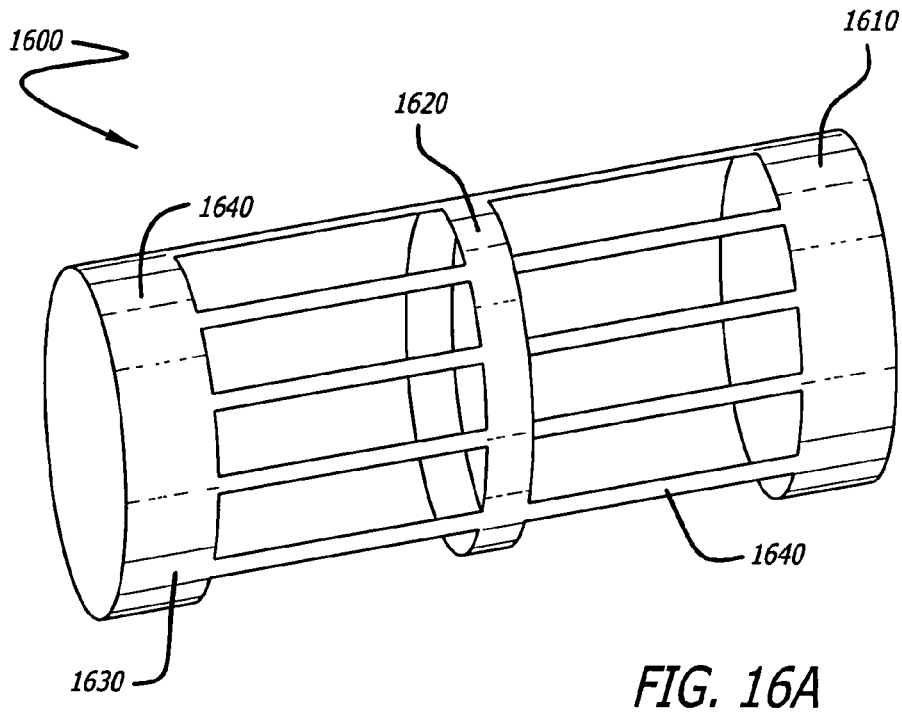
FIGS. 16A and 16B are cage mechanism in accordance with the present invention for use with the fiber bundle.
Figure 16B:
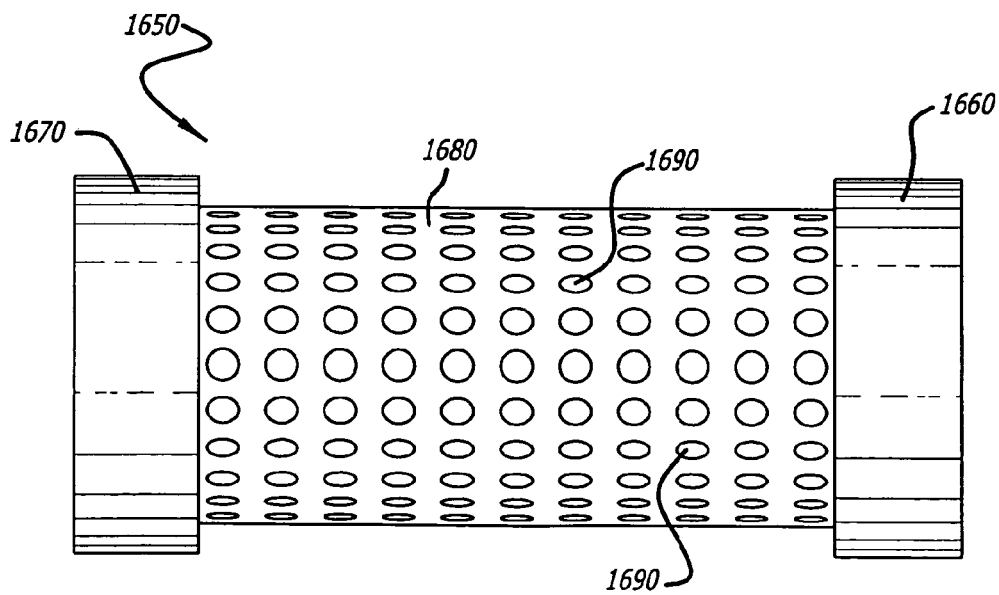

Referring now to FIGS. 2A, 2B and 2C, one embodiment of the paracorporeal respiratory assist lung 20 of the present invention includes an outer housing 22 surrounding a stationary core 24. A rotating fiber bundle 26 is contained within the outer housing and around the stationary core. A motor drive mechanism 28 is operably connected to the main housing of the paracorporeal respiratory assist lung. The stationary core includes a main body 30 having a blood inlet port 32 that allows blood to diffuse from the stationary core through a fiber mat 40 of the rotating fiber bundle. The outer housing is further configured with a blood outlet port 34 that, along with the blood inlet, may be connected to a cannula (not shown) configured to be inserted into the patient vasculature (FIG. 1). The outer housing is further configured with a gas inlet nozzle 36 and a gas outlet nozzle 38 that are in fluid communication with the fiber mat of the rotating fiber bundle. The fiber mat is fixedly connected to a support mechanism 42 that is connected to a drive shaft 44 that is operably connected to the motor drive mechanism. The support mechanism for the fiber mat may be configured as a wire or mesh cage (FIGS. 16A, 16B) or other suitable embodiments to enhance blood flow through the fiber bundle while minimizing any damage to the blood components, e.g., limiting hemolysis.

Referring now to FIGS. 3A, 3B, 3C and 3D, the paracorporeal respiratory assist lung 50 of the present invention includes a central outer housing 52 having a blood outlet port 64. A first end portion 54 of the outer housing includes a blood inlet port 62 and a gas inlet nozzle 66. A second end portion 58 of the outer housing includes a gas outlet nozzle 68. The first and second ends of the housing may be configured with threads or other mechanism to secure the ends of the housing to the central portion. A rotating fiber bundle mechanism 56 is configured to be disposed within the housing and includes a support mechanism (not shown) for retaining the fiber bundle while allowing blood to flow from the housing inlet through the fibers. The fiber bundle may be formed from an annular fiber mat 60 that is in fluid communication with the gas inlet and the gas outlet. The rotating fiber bundle mechanism further includes a drive shaft 74 that may be mechanically connected to a motor mechanism (not shown). The rotating fiber bundle mechanism may be further configured with a potting 72 to hold the ends of the fibers of the fiber mat.

Figure 4A:
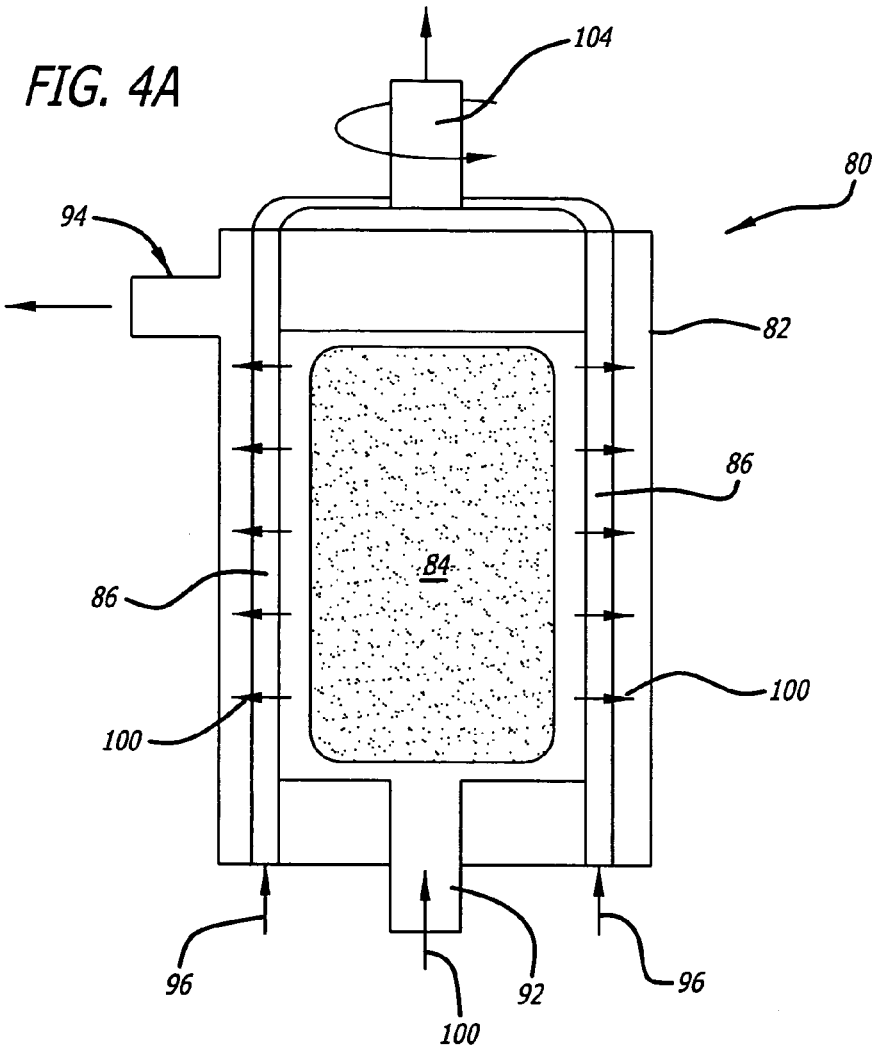
FIGS. 4A and 4B are schematic representations of the paracorporeal respiratory assist lung of the present invention showing a rotating bundle.
Figure 4B:
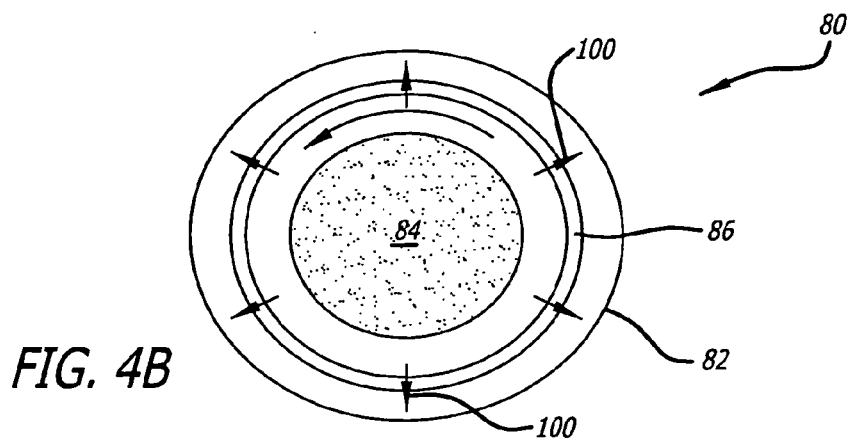
Figure 21:
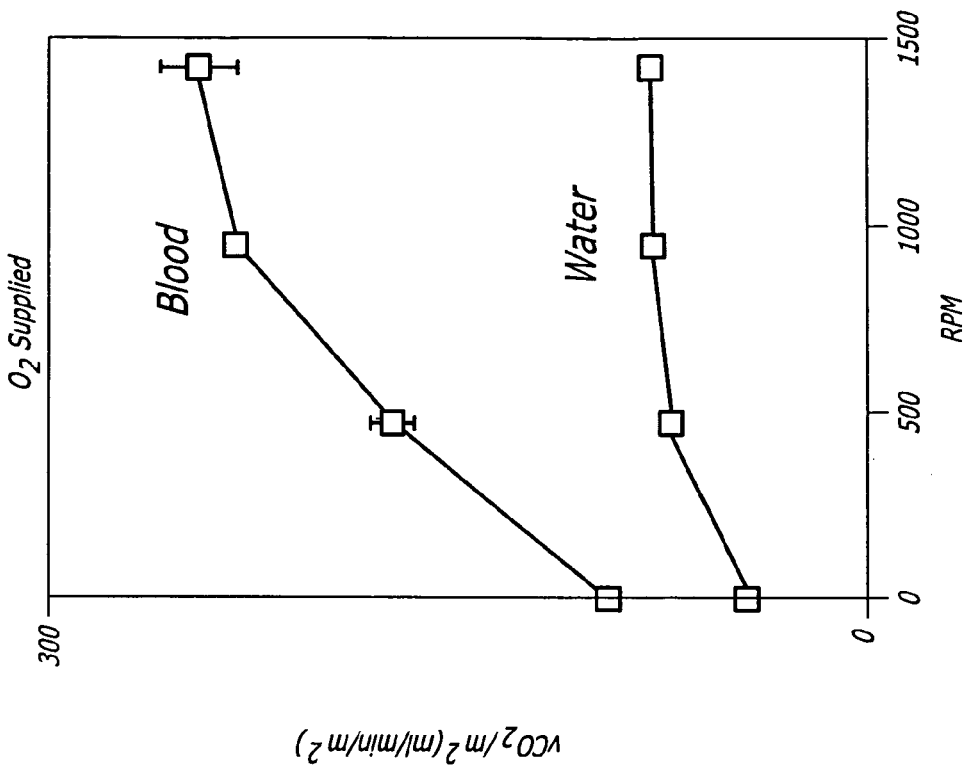
FIG. 21 is a graphical representation of gas exchange rates achieved with an embodiment of a paracorporeal respiratory assist lung of the present invention.
Figure 20:
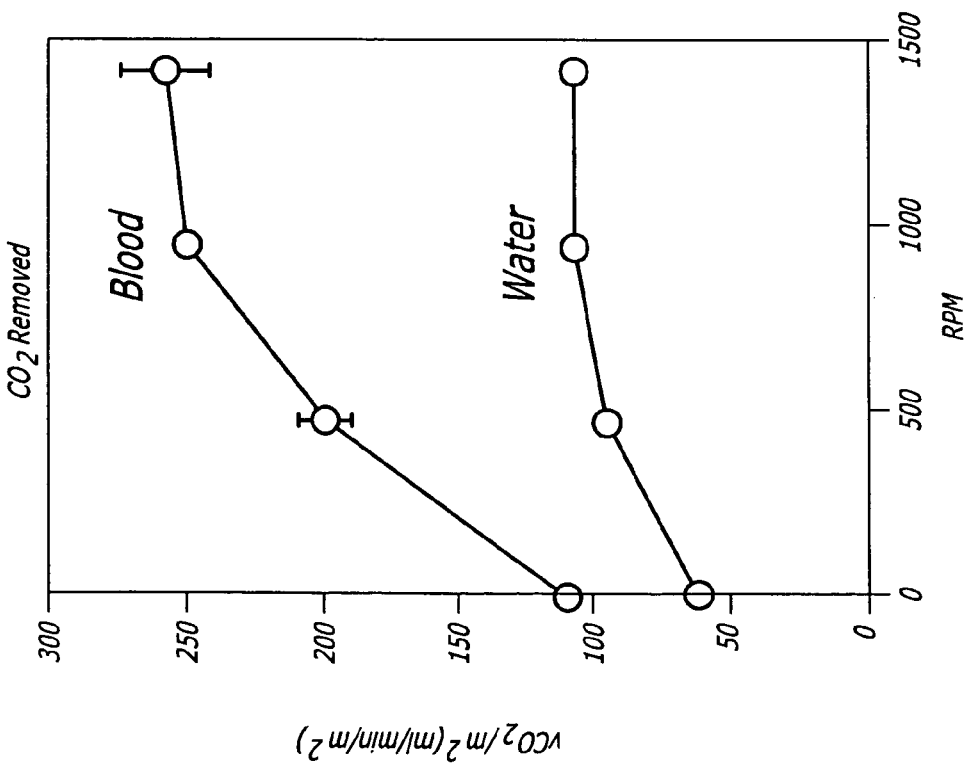
FIG. 20 is a graphical representation of gas exchange rates achieved with an embodiment of a paracorporeal respiratory assist lung of the present invention.
Figure 22:
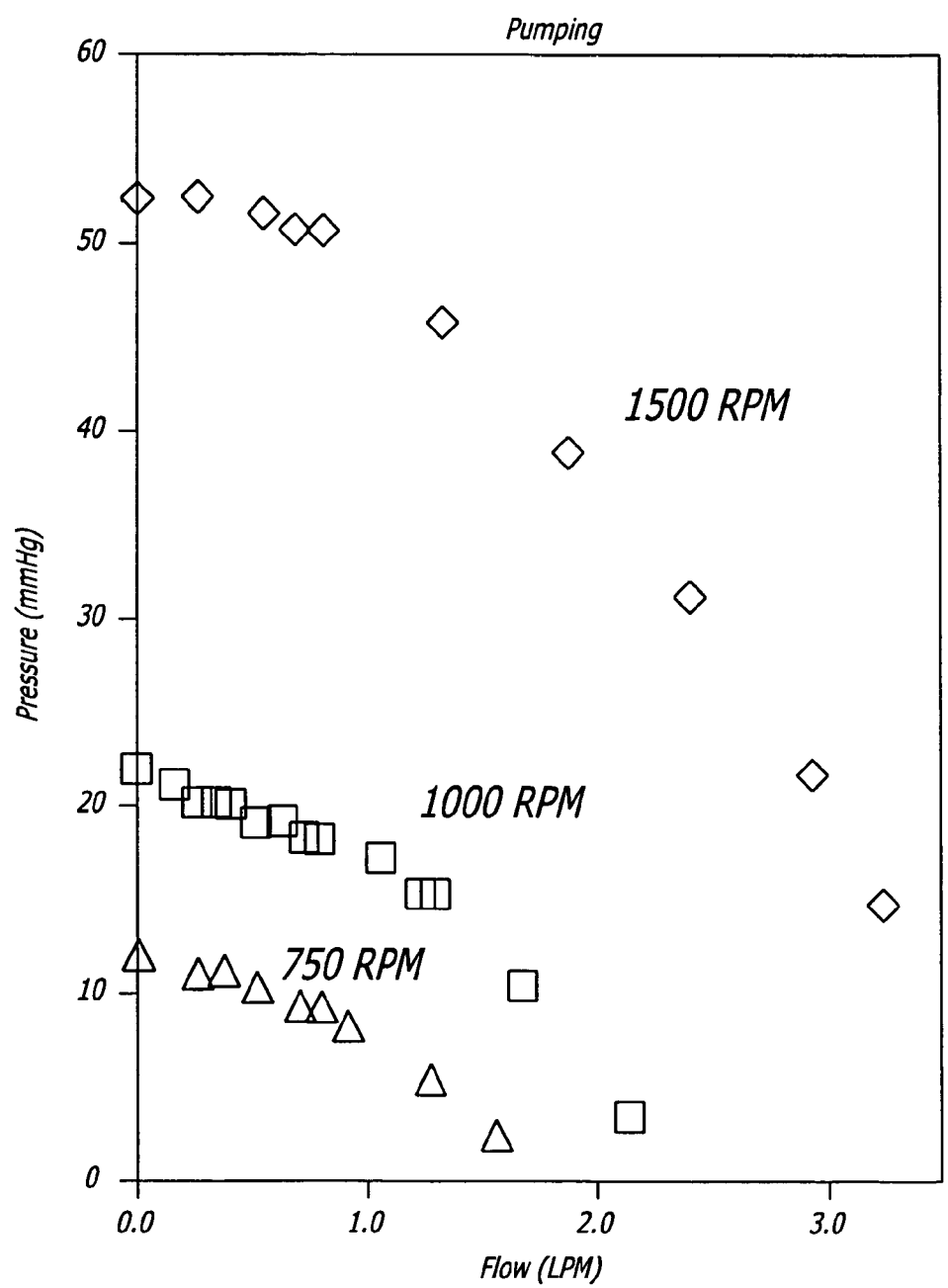
FIG. 22 is a graphical representation of blood flow (pumping) achieved with an embodiment of a paracorporeal respiratory assist lung of the present invention.

Referring now to FIGS. 4A and 4B, the paracorporeal respiratory assist lung 80 used for testing purposes generally is configured with an outer housing 82 that surrounds a rotating fiber bundle 86 having a stationary core 84 disposed with the fiber bundle and the housing. Blood 100 enters the device through an inlet port 92 of the stationary core. Oxygen laden sweep gas 96 enters the rotating fiber core so that oxygen and carbon dioxide are exchanged to and from the blood along the fiber bundle. The rotating fiber bundle is configured with a drive shaft 104 for rotating the fiber bundle relative to the stationary core and outer housing. Referring to FIGS. 20, 21 and 22, typical experimental conditions using the paracorporeal respiratory assist lung of the present invention that achieved (a) increased $CO_2$ removal per area by 133%; (b) increased $O_2$ removal per area by 157%; and (c) generated 1 l/min flow against fifty mmHg at 1500 rpm include: (i) test fluid of water or slaughterhouse bovine blood; (ii) fluid flow rate at 750 ml/min; (iii) sweep gas flow rate at 6.5 l/min; (iv) loop temperature at 37° C.; (v) inlet $pCO_2$ at 45+/−5 mmHg; (vi) inlet $O_2$ saturation at 65%; (vii) blood hematocrit at 35%; and (viii) blood hemoglobin concentration at 12.1 milligrams per deciliter (mg/dl).

A hollow fiber membrane bundle that has an annular cylindrical geometry can function as a pump when the bundle is rotated. Fluid in the bundle, however, becomes significantly entrained in the fiber rotational motion (the relative velocity between the fibers and the fluid goes to zero), and hence the rotation does not increase mass transfer efficiency for fiber bundles more than a few layers thick. A hollow fiber membrane bundle can be oscillated to reduce the entrainment of fluid because oscillation hinders the fluid velocity from reaching the fiber velocity. One aspect of the present invention is to introduce oscillations in the steady rotation of a hollow fiber bundle to increase the mass transfer efficiency of the device while maintaining its pumping capabilities.

Figure 18:
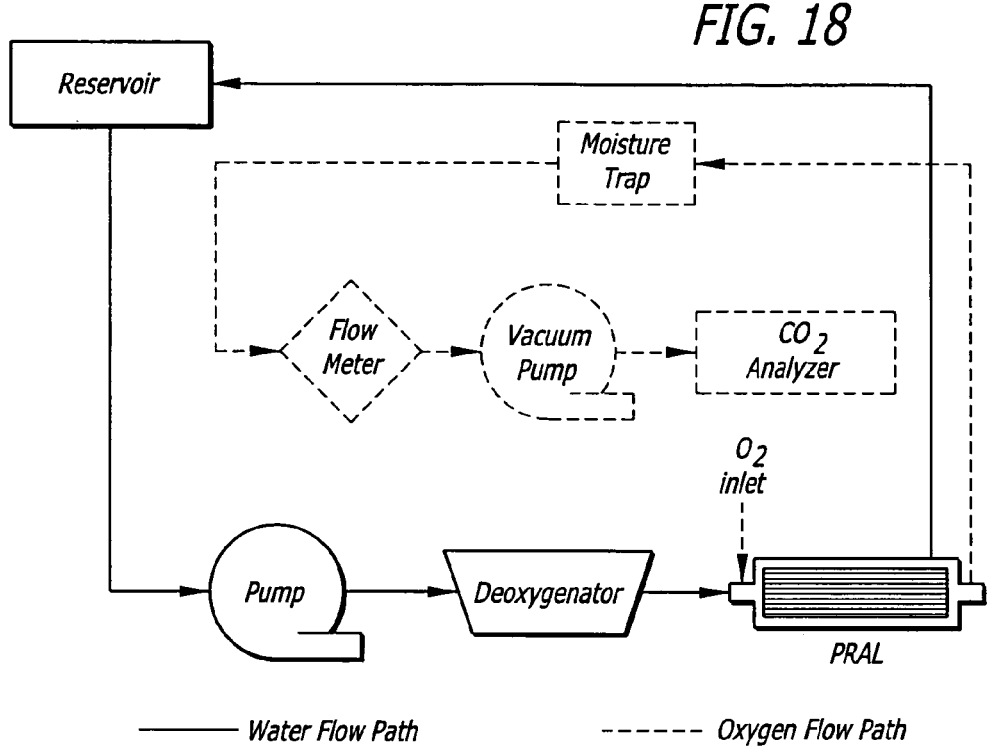
FIG. 18 is a block diagram in accordance with the system of the present invention.
Figure 19:
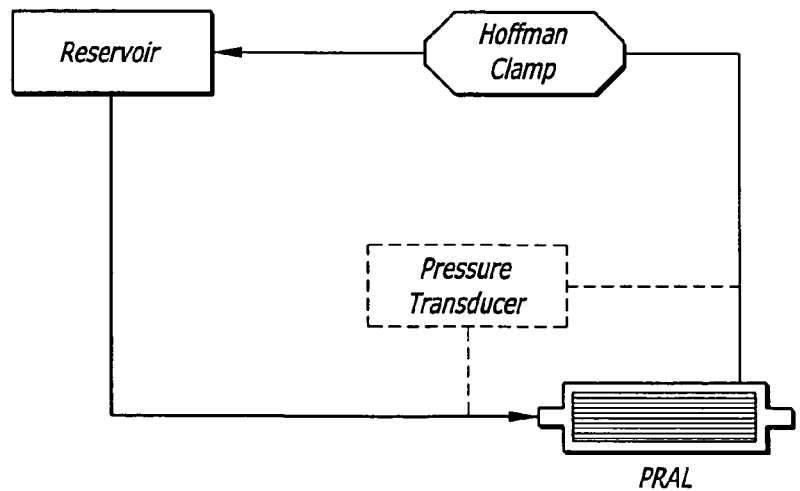
FIG. 19 is a block diagram in accordance with the system of the present invention.

As shown in FIGS. 18 and 19, the paracorporeal respiratory assist lung of the present invention acts as an integrated pump/hollow fiber membrane mass transport device, and shows mass transfer enhancement when the rotational velocity of the fiber bundle is rapidly varied. To enhance performance of the gas exchange achieved by the paracorporeal respiratory assist lung, various modes of spinning the fiber bundle may be employed, e.g., steady rotation, unsteady rotation, purely oscillatory rotation and other forms of time-dependent rotation. As will be appreciated by those of ordinary skill in the art, known and to-be-developed gas-permeable fibers may be used with the present invention, for example, hollow microporous polypropylene fibers and gas-permeable fibers currently used in blood oxygenators. The gas-permeable fibers may include a coating of a gas-permeable polymer and may be bonded with a non-thrombogenic component.

The rotation actuator device may include a motor that is coupled to the fiber bundle. Oxygen is passed through the hollow fibers, and fluid (e.g., water or blood) may be introduced to the fiber bundle through an internal diffuser. Seals and bearings separate the gas and fluid pathways and allow the fiber bundle to be rotated with an external motor. A brushless DC servomotor may control the motion of the hollow fiber membrane bundle. The user of the paracorporeal respiratory assist lung may set the frequency and amplitude of oscillation with a computer connected to a controller. The controller signals a drive to perform the input motion while getting feedback from the motor and making adjustments to the velocity.

In a further embodiment of the present invention, the paracorporeal respiratory assist lung is configured to increase the porosity in the rotating fiber bundle. The increased porosity provides more fluid to flow through the fiber bundle, thus increasing the overall mass transfer efficiency of the device. The extra porosity in the fiber bundle is created by several possible ways including, but not limited to, using spacers to create void space between the fiber layers, removing every other fiber in the mat and using smaller diameter fibers. Additionally, support threads could be removed from the fiber fabric, and the paracorporeal respiratory assist lung could be configured such that the manifolds are relatively closer so as to "puff out" the fiber bundle.

Figure 17A:
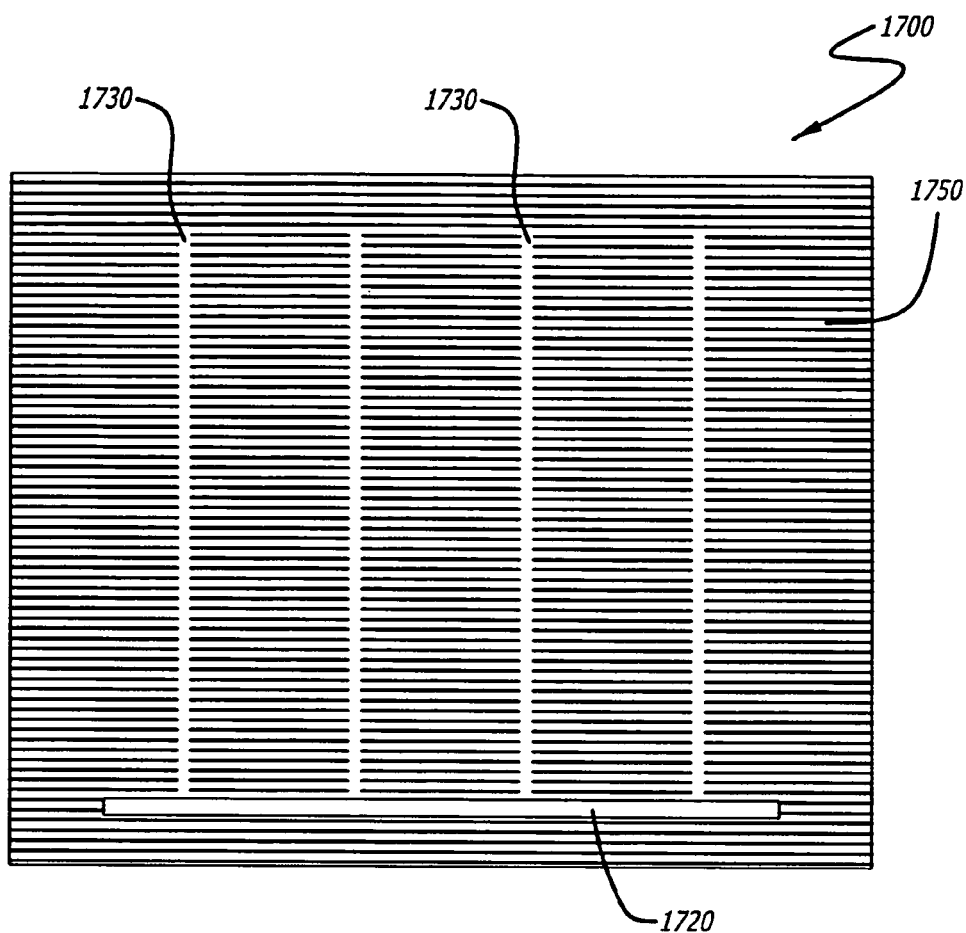
FIGS. 17A, 17B depict schematic representations of a fiber mat having spacers for use in the paracorporeal respiratory assist lung of the present invention.
Figure 17B:
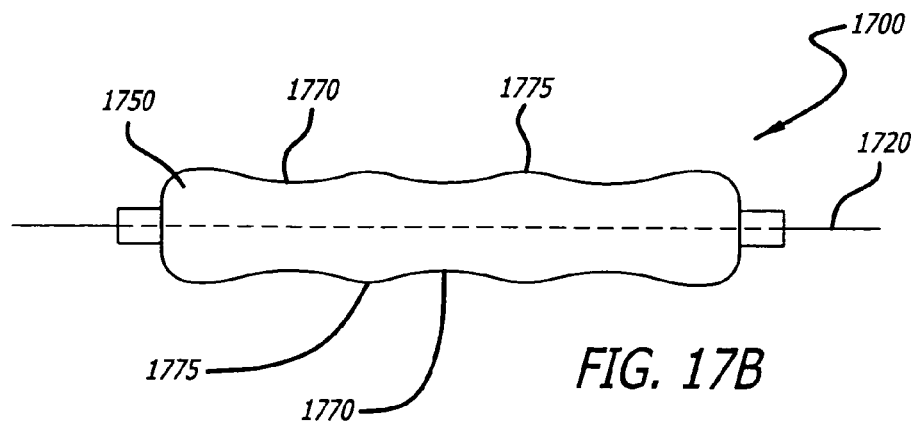

As shown in FIGS. 17A and 17B, spacers can be created by placing thin strips of felt that are soaked in polyurethane or other suitable material across a fiber mat. In accordance with the present invention, as the fiber mat is rolled up, the felt is rolled with it, which then hardens as the adhesive dries. The dried felt then creates the extra space between the fibers. However, the fiber surface area where the felt is touching is not included in the operable surface area of the paracorporeal respiratory assist lung. Alternatively, by removing every other fiber in the fiber mat, the fiber mat is left with many open spaces having only wefts and no fibers. The same overall surface area and number of fibers may be the same, but the fibers are much more spaced out, thus creating a "puffy bundle." Further, gas-permeable fibers having a reduced outer diameter can also be used to create higher porosity devices. The higher porosity of the fiber bundle results from a reduced fiber density, i.e., the fiber density in a mat of smaller outer diameter fibers is less than fiber mats having larger outer diameter fibers. There is much more open space where only wefts exist, similar to configurations of the fiber bundle where every other fiber is removed.

Figure 23:
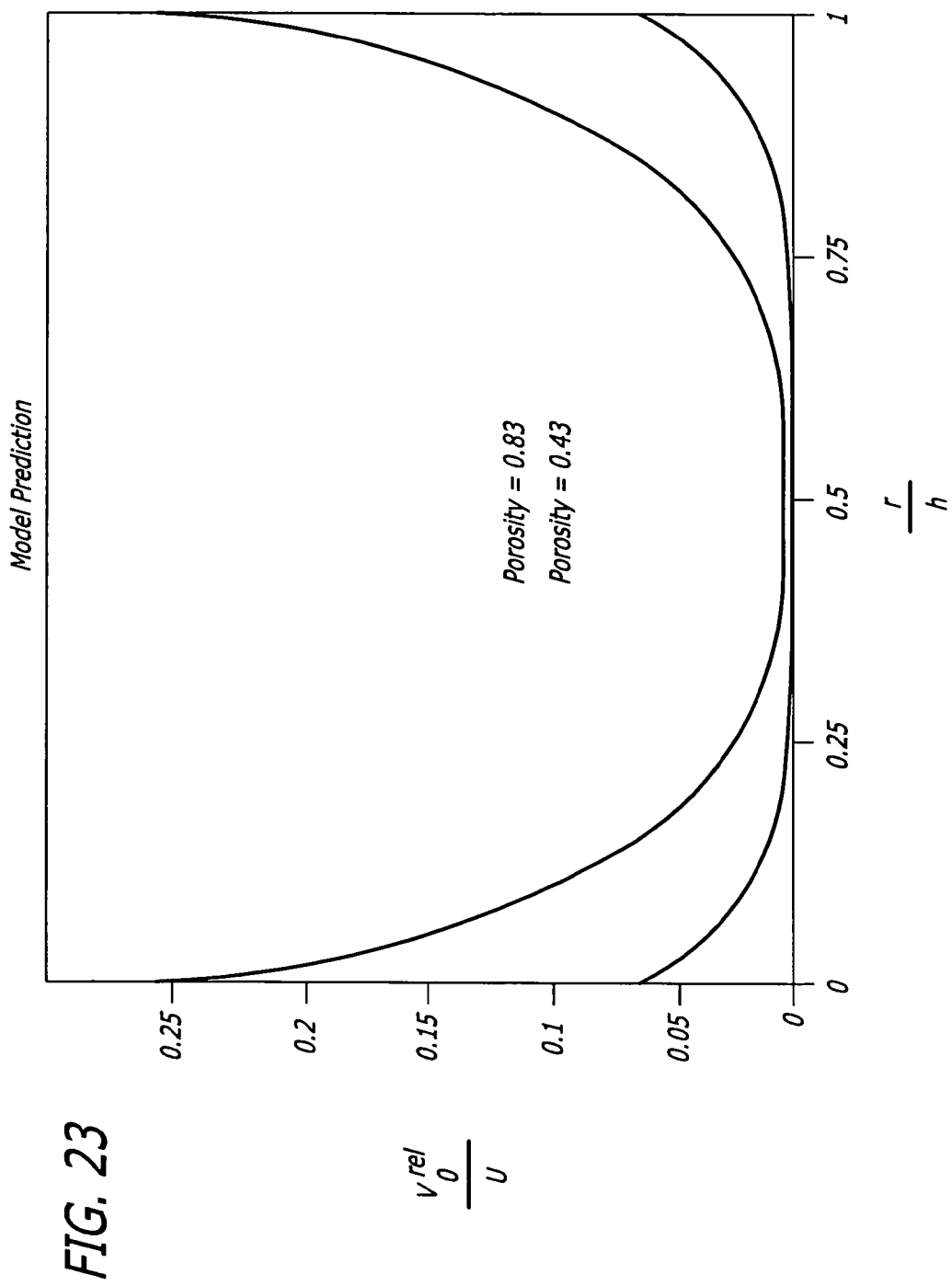
FIG. 23 is a graphical representation of a model prediction based on the porosity of the fiber bundle.
Figure 25:
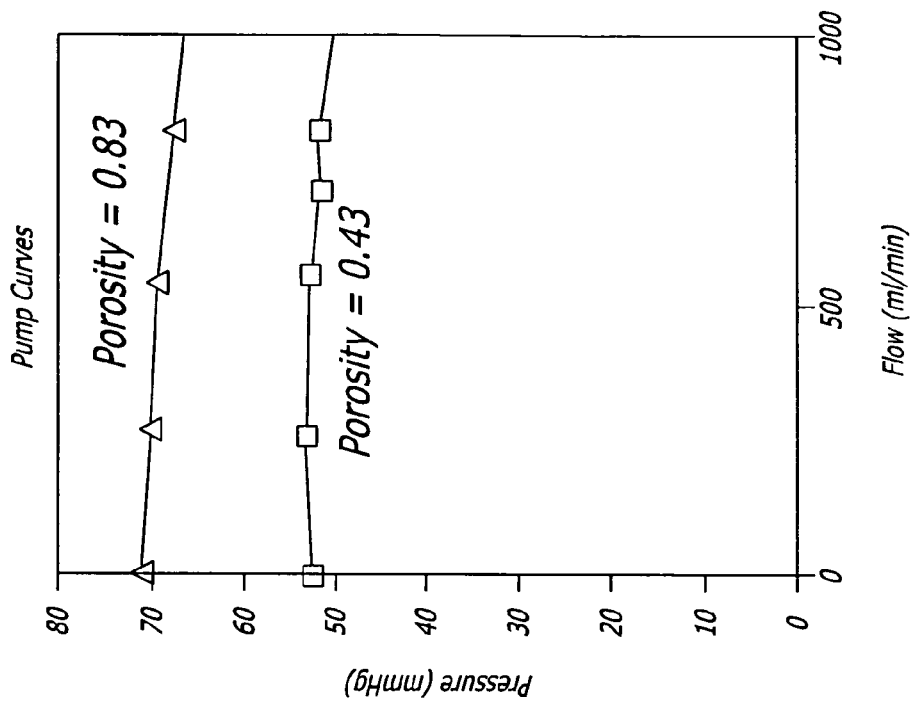
FIGS. 24 and 25 are graphical representations of carbon dioxide removal and blood flow (pumping) achieved with varied porosity of the fiber bundle in the paracorporeal respiratory assist lung of the present invention.
Figure 24:
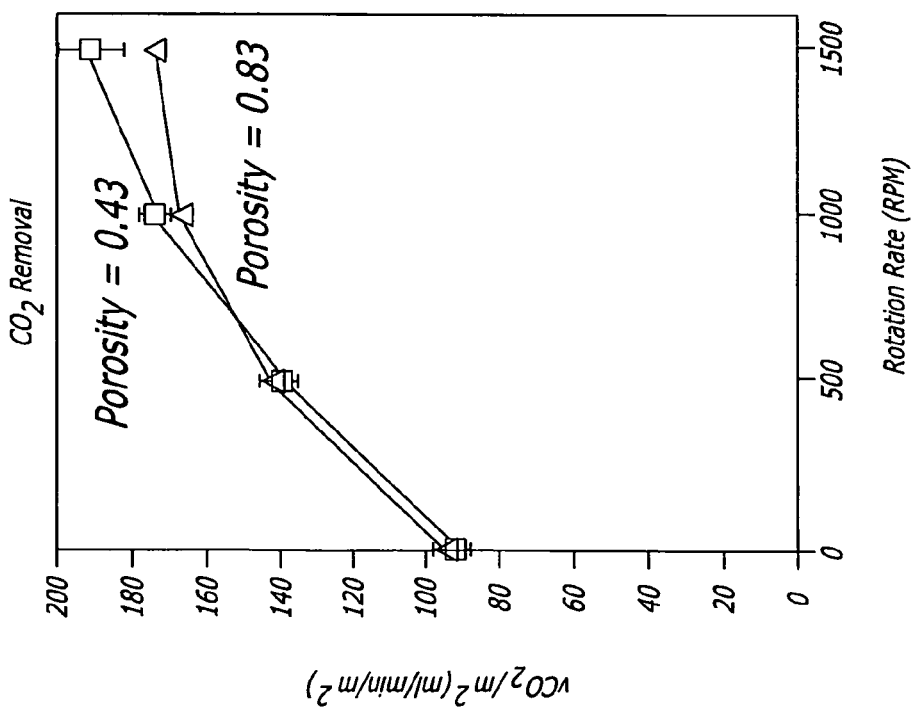

The paracorporeal respiratory assist lung of the present invention achieves significant $CO_2$ removal (100-120 ml/min) at relatively low veno-venous blood flow rates (500-1000 ml/min) without the need for a separate pump. FIGS. 23-25 demonstrate the effect of fiber bundle porosity on the gas exchange and pumping performance of the paracorporeal respiratory assist lung. Two prototype paracorporeal respiratory assist lung devices were fabricated with bundle porosities of 0.43 and 0.83, but otherwise similar with membrane areas of 0.42 square meters ($m^2$) and 0.50 $m^2$ respectively. The devices were tested for gas exchange in a flow loop using water as the test fluid at three l/min. The paracorporeal respiratory assist lung prototype with the higher bundle porosity achieved $CO_2$ removal at 1500 rpm of 173 ml/min/$m^2$ compared to 190 ml/min/$m^2$ for the prototype with the lower bundle porosity. In bovine blood, the paracorporeal respiratory assist lung with the higher bundle porosity at 1500 rpm achieved a $CO_2$ removal rate of 182 ml/min/$m^2$ at a blood flow rate of only 750 ml/min. In a separate pump test in water, the fiber bundle with higher porosity generated 67 mmHg compared to only 52 mmHg for the fiber bundle with the lower porosity at 0.75 l/min flow at 1500 RPM with water as the test fluid. The fiber bundle with increased porosity is within ten percent of a gas exchange target, and the pumping ability is consistent with generating 750 ml/min blood flow through percutaneous cannula less than 20 Fr.

Figure 5D:
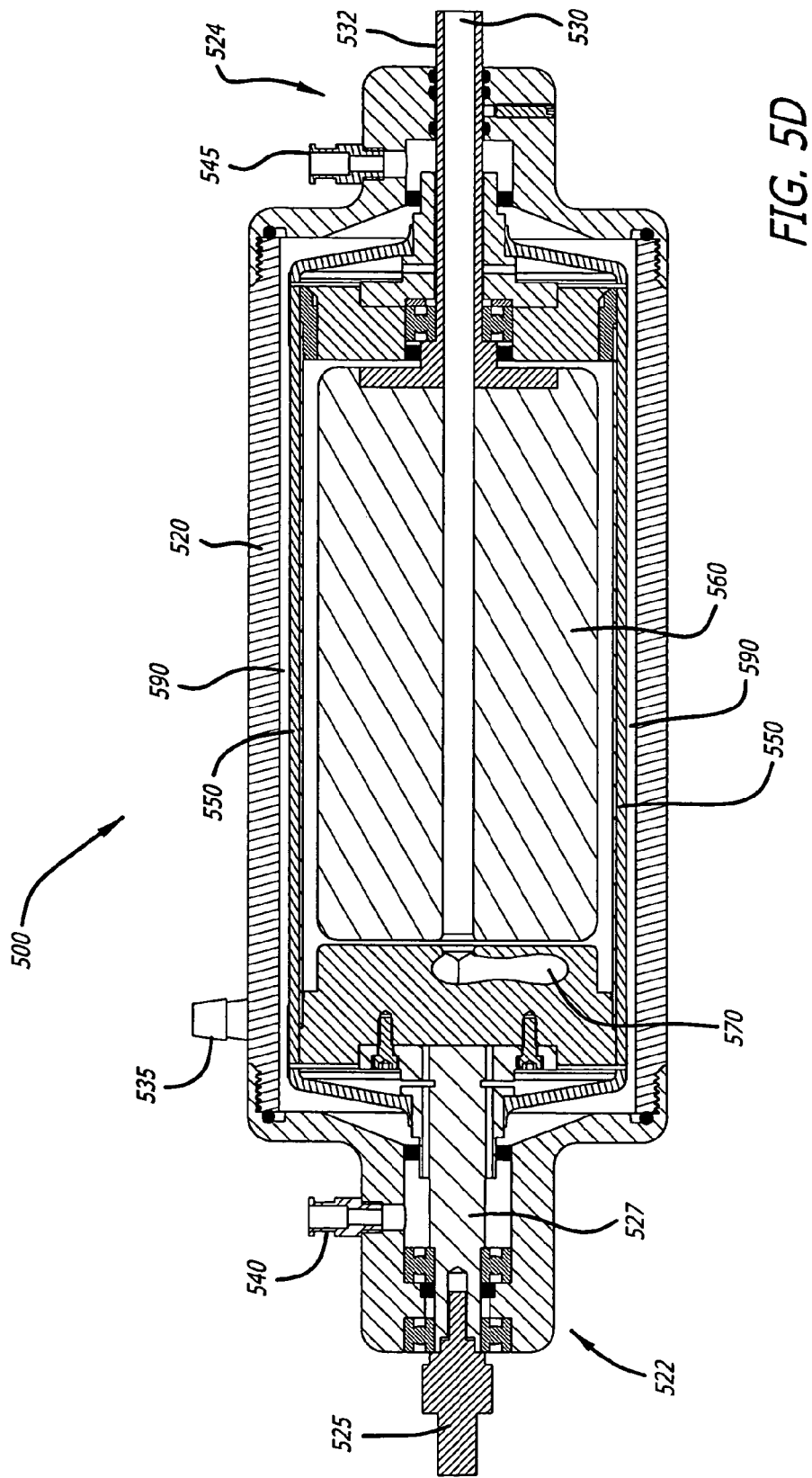
FIGS. 5A-5P depict several views of an alternative embodiment of the paracorporeal respiratory assist lung of the present invention.
Figure 5F:
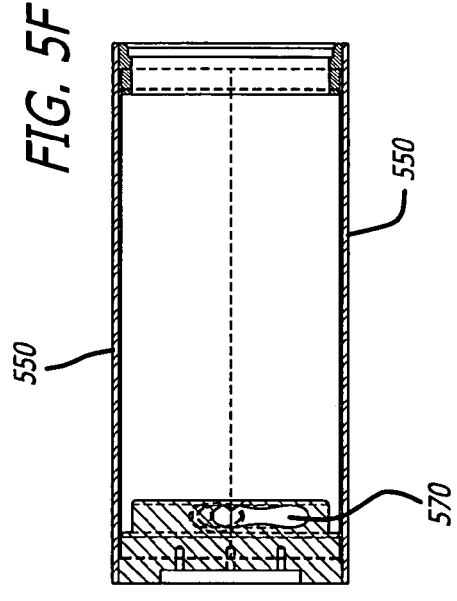
Figure 5H:
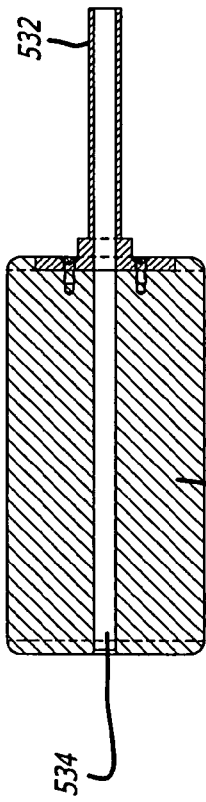
Figure 5E:
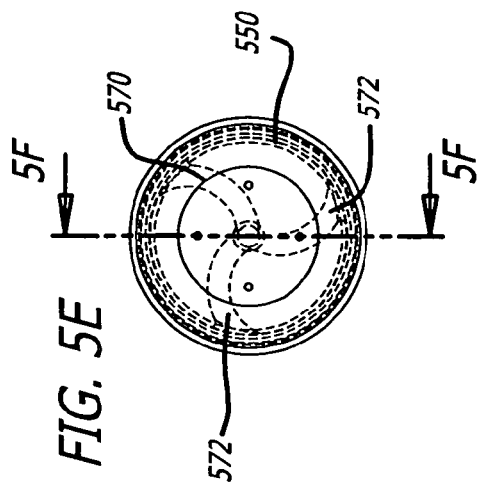
Figure 5G:
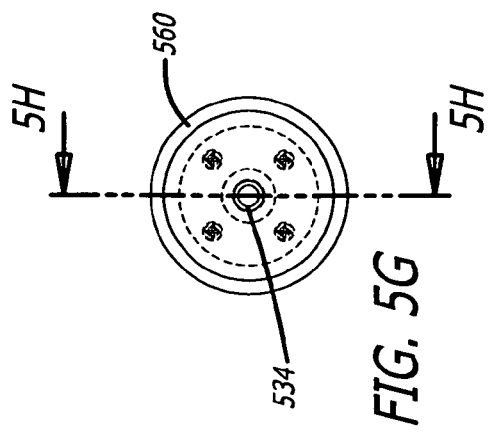
Figure 5J:
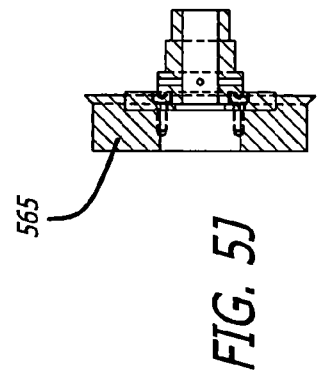
Figure 5L:
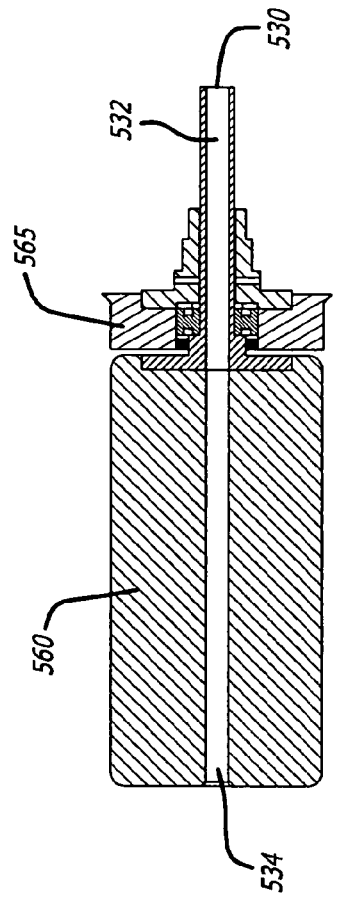
Figure 5I:
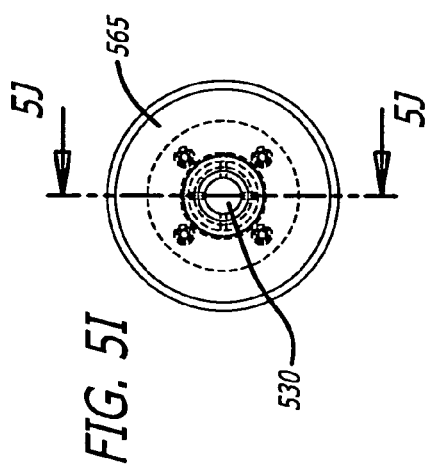
Figure 5K:
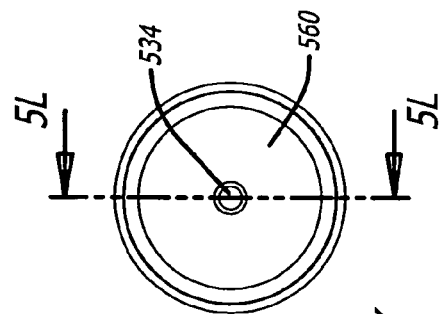

Referring now to FIGS. 5A through 5P, one embodiment of the PRAL device includes an outer housing 520 having an upper portion 524 and a lower portion 522. The upper portion of the PRAL device 500 includes a blood inlet 530 and a gas outlet 545. The lower portion of the housing includes a gas inlet 540 and a blood outlet port 535. This embodiment of the PRAL device includes a rotating fiber bundle having an external drive connection 525. As shown in FIG. 5D, the drive mechanism 525 is connected to an internal coupling 527 that can exit to the fiber bundle 550. The PRAL device includes a stationary core 560 that is configured with a lumen or blood conduit having an outside end 532 and an inside end 534. The inside end of the blood conduit is attached to an impeller device 570 which may include a plurality of arcuate arms 572 that assist in directing blood flow through the fiber bundle 550. The PRAL device is configured with an annular space 590 between the rotating fiber bundle 550 and the outer housing 520. Blood flow commencing at the entrance 530 and traveling from the impeller 570 through the fiber bundle 550 and gap 590 exits through the port 535. Sweep gas, such as oxygenated air, enters the PRAL device through entry port 540 travels through the fiber bundle 550 wherein carbon dioxide and oxygen are exchanged with the blood and the carbon dioxide laden gas exits through the port 545 in the upper portion 524 of the PRAL device. The upper portion of the PRAL device is further configured with a retaining device 565 that secures the core 560 and blood conduit 530 within the housing 520.

Figure 6:
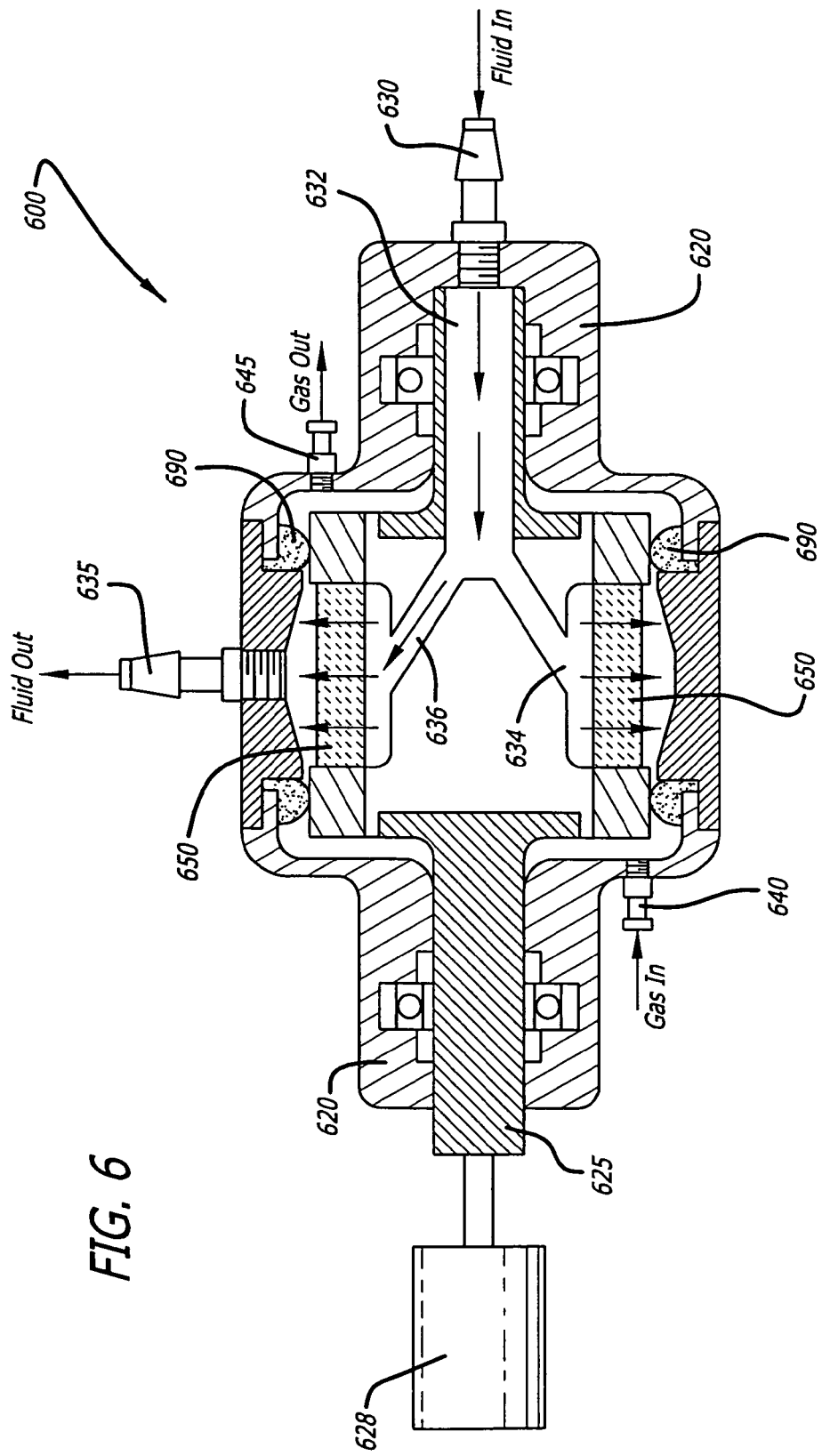
FIG. 6 depicts an alternative embodiment of the paracorporeal respiratory assist lung of the present invention.

Referring now to FIG. 6, an alternative embodiment of the PRAL device 600 includes an outer casing 620 having a blood and fluid inlet 630 and fluid outlet 635 passes through the inlet through a conduit 632 that bifurcates into a first conduit 634 and a second conduit 636 that direct blood through the fiber bundle 650. The fiber bundle is connected to a drive mechanism 625 that is connected to a motor drive 628. A plurality of sealing mechanisms 690 are included to separate the rotating fiber bundle and blood flow from the gas pathway. Gas enters the system through inlet 640 that is connected to the fiber bundle and exits through the gas outlet port 645 in fluid communication with the fiber bundle 650.

Figure 7:
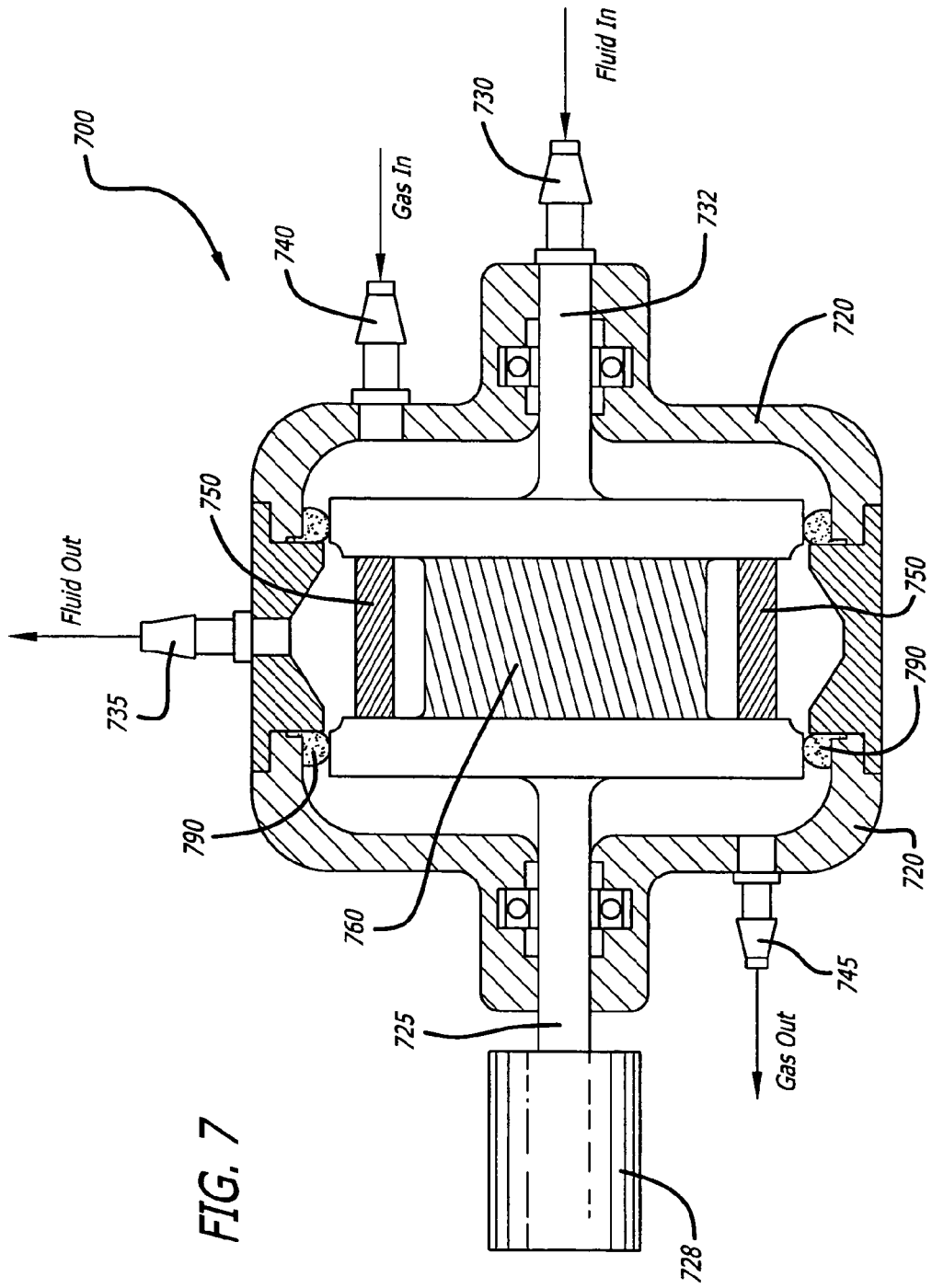
FIG. 7 depicts an alternative embodiment of the paracorporeal respiratory assist lung of the present invention.
Figure 8A:
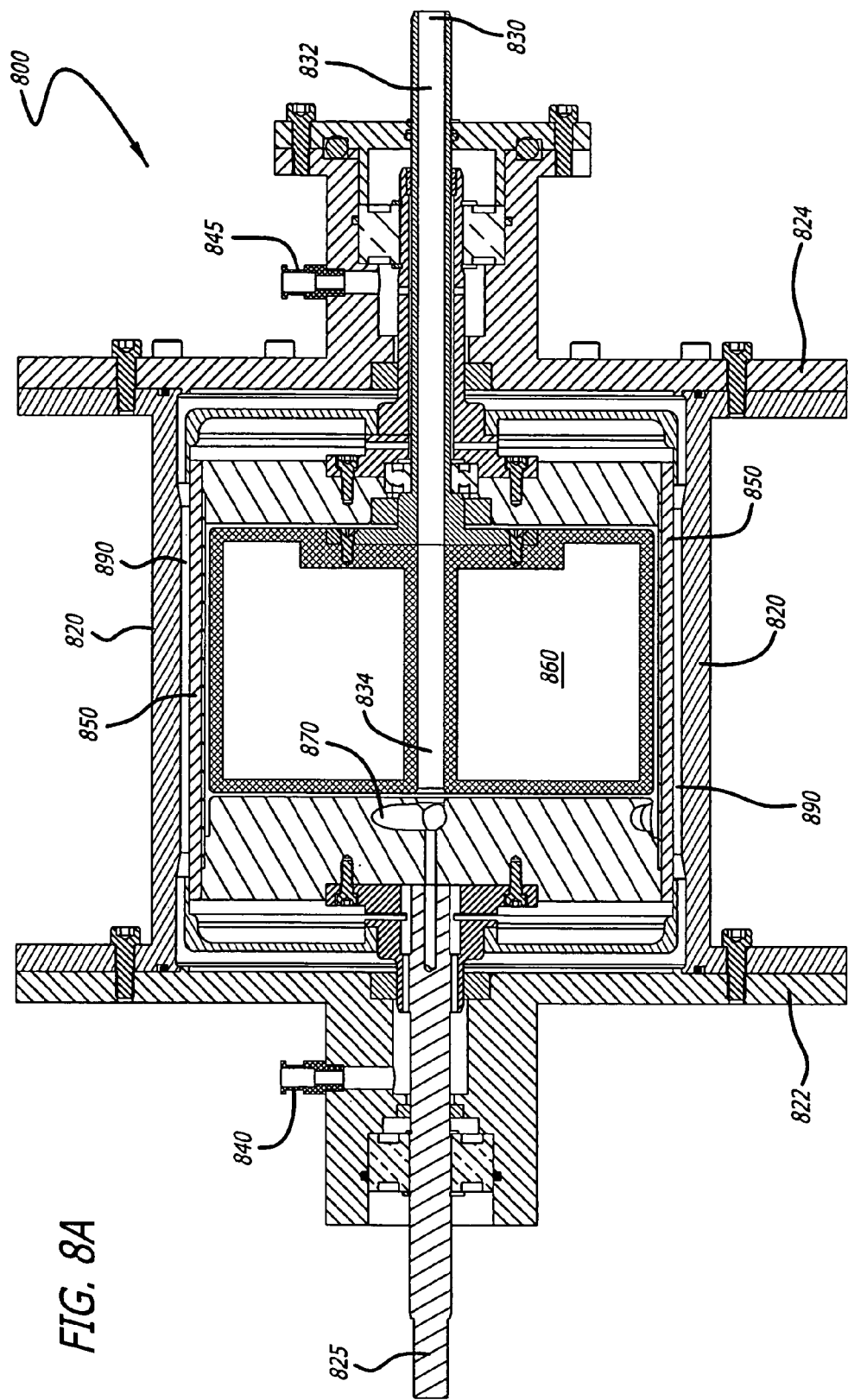
FIGS. 8A-8D depict several views of an alternative embodiment of the paracorporeal respiratory assist lung of the present invention.
Figure 8B:
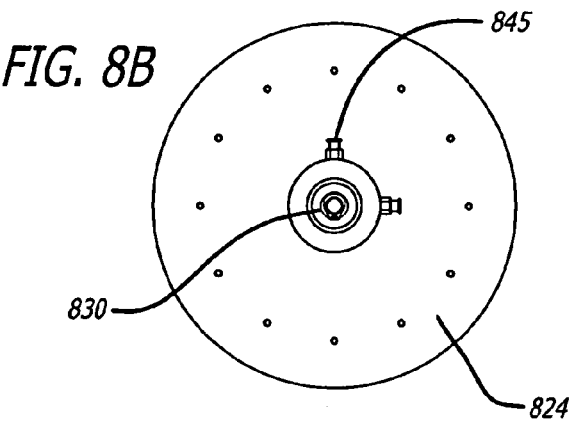
Figure 8C:
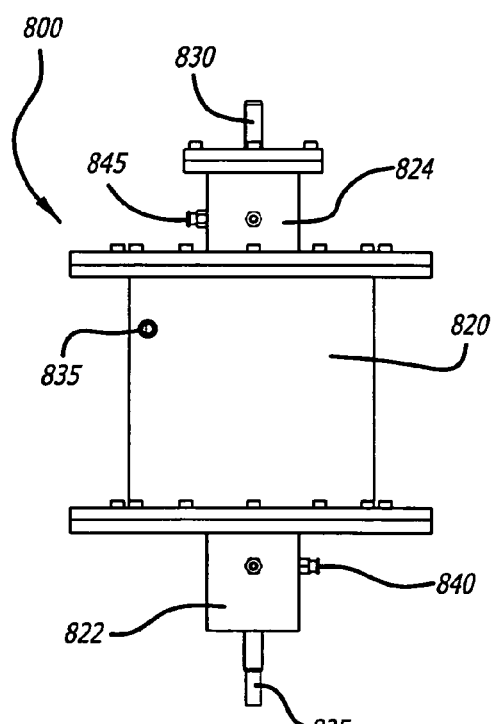
Figure 8D:
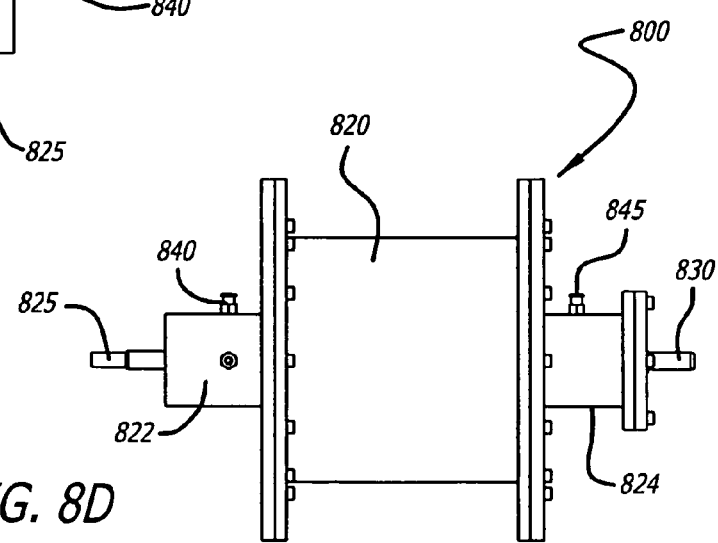

Referring now to FIG. 7, an alternative embodiment of the PRAL device 700 includes an outer casing 720 having a blood and fluid inlet 730 and fluid outlet 735 passes through the inlet through a conduit 732 that directs blood through the fiber bundle 750. The fiber bundle is connected to a drive mechanism 725 that is connected to a motor drive 728. A plurality of sealing mechanisms 790 are included to separate the rotating fiber bundle and blood flow from the gas pathway. Gas enters the system through inlet 740 that is connected to the fiber bundle and exits through the gas outlet port 745 in fluid communication with the fiber bundle 750. This particular embodiment further includes a stationary core 760 positioned inside of the rotating fiber bundle 750.

Referring now to FIG. 8 is an alternative embodiment of the PRAL device 800 in accordance with the present invention. The PRAL device includes an outer shell 820 having a lower portion 822 and an upper portion 824 secured to the main body 820. The upper portion of the device includes a blood inlet 830 connected to a conduit 832 having a distal end 834 for providing blood flow through a central core 860 and an impeller 870. The blood flow passes through a rotating fiber bundle 850 that is connected to a drive mechanism 825. Gas enters from the lower portion 822 of the housing through an inlet gas port 540 that is in fluid communication with the fiber gas bundle 850 and an exit gas port 845. A small annular gap 890 resides between the rotating fiber bundle 850 and the outer housing 820 of the device 800. Various seals and other mechanisms are used to isolate the gas flow from the blood flow. Similarly, screws and other mechanisms are used to secure the portions of the housing. In addition various seals and bearings are used to allow the drive mechanism and rotating core to freely move within the housing.

Figure 9:
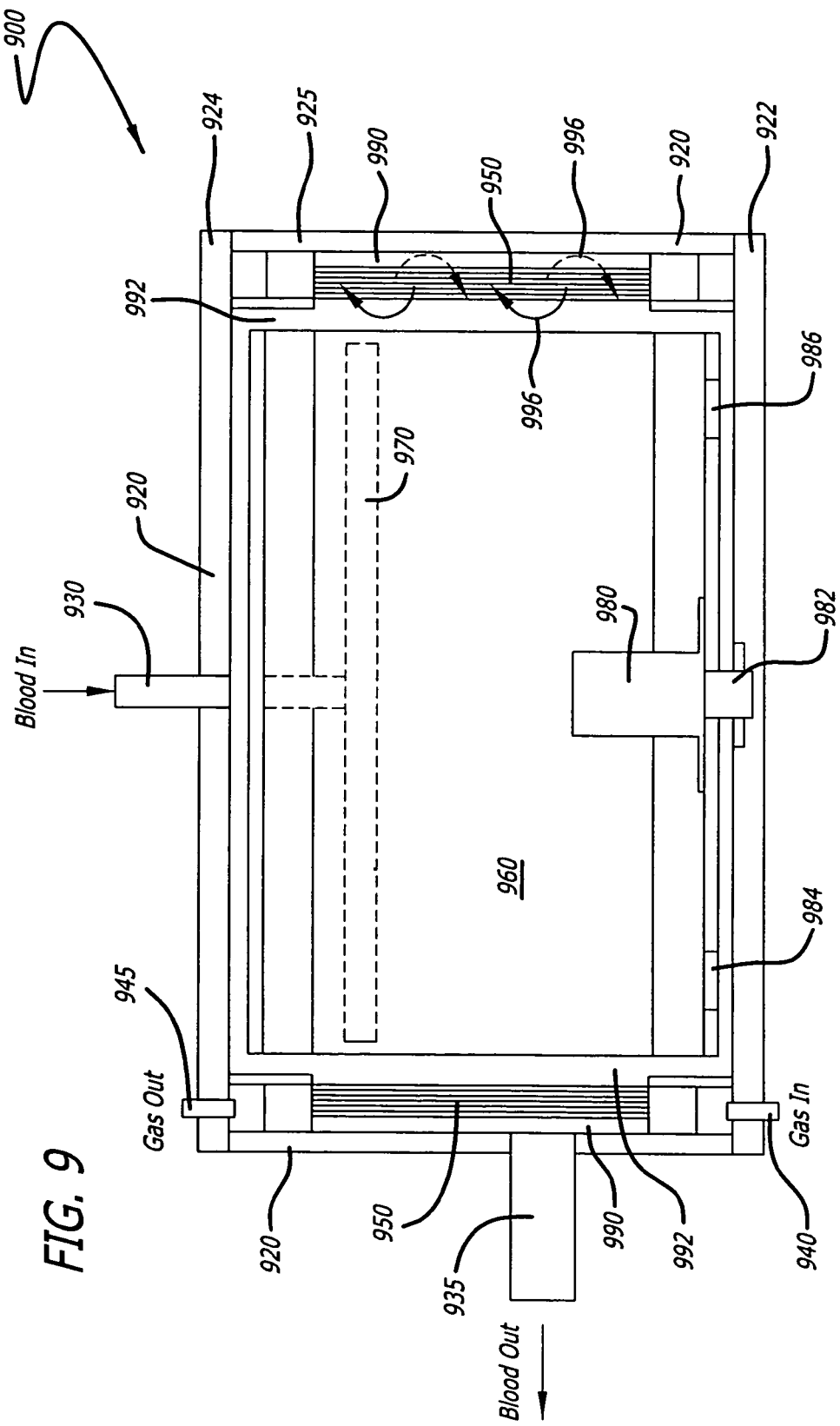
FIG. 9 depicts schematic view of an alternative embodiment of the paracorporeal respiratory assist lung of the present invention having a magnetic drive mechanism.

Referring now to FIG. 9, an alternative embodiment of the PRAL device 900 in accordance with the present invention includes magnetic couplings for rotating a central core. The PRAL device includes a housing 920 having a lower portion 922 and an upper portion 924. The upper portion includes a blood inlet conduit 930 that is connected to a blood distribution impeller 970 embodied within the rotating core 960. The lower portion of the body 922 includes seals and bearings 980 and a pin or other mechanism 982 for the rotating core to rest within the housing. This embodiment of the PRAL device includes a stationary fiber bundle 950 having a gas inlet 940 and a gas outlet 945. Blood flows from the inlet 930 through an internal gap 922 past the bundles 950 through a recirculation gap 990 and out the blood exit port 935. The internal and recirculation gaps between the rotating core and the outer housing allow for a recirculation or eddy effect shown by arrows 996. The rotating core is magnetically coupled to an external device via magnets 984 and 986 secured to the rotating core.

Figure 10A:
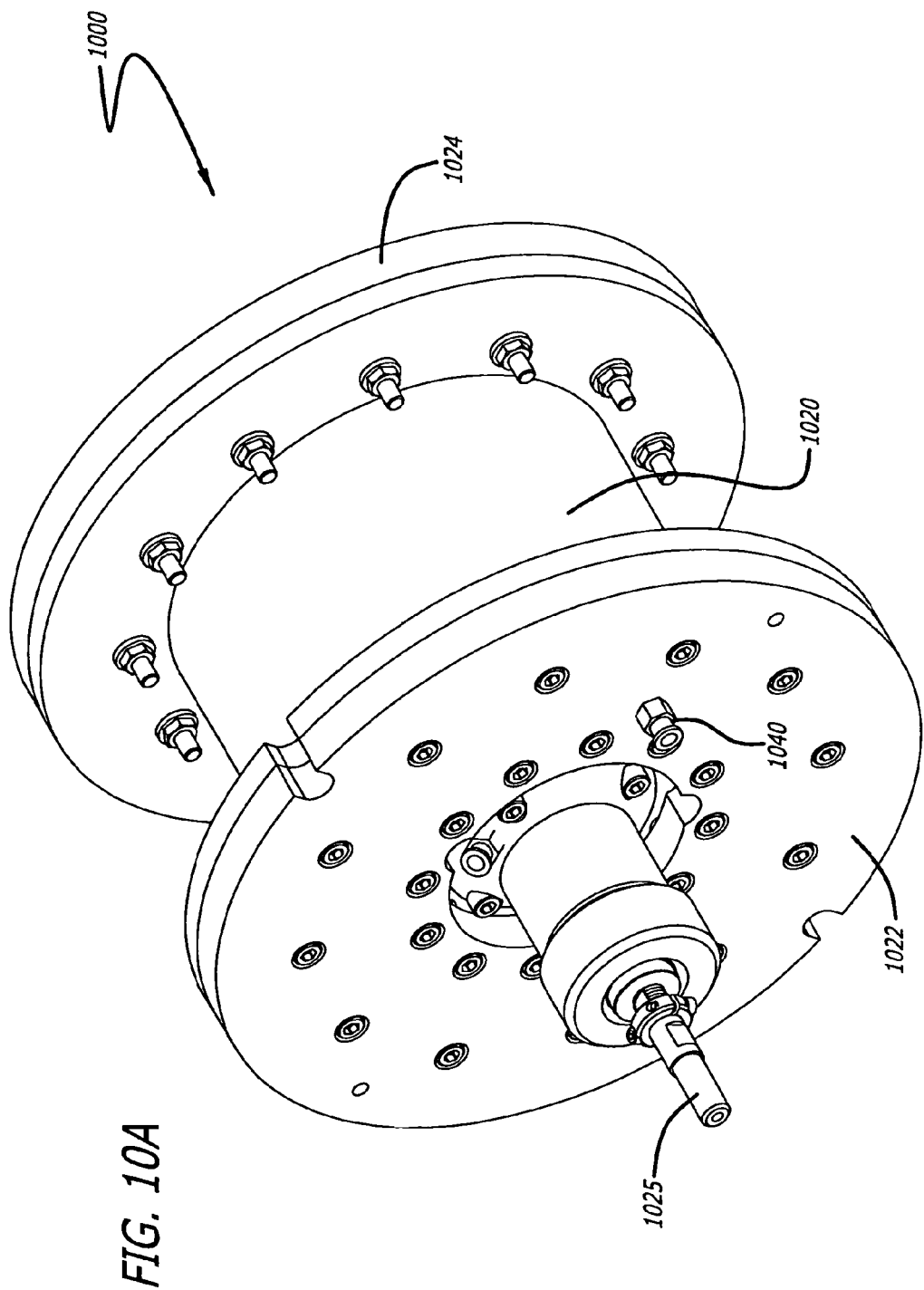
FIGS. 10A and 10B depict an alternative embodiment of the paracorporeal respiratory assist lung of the present invention.
Figure 10B:
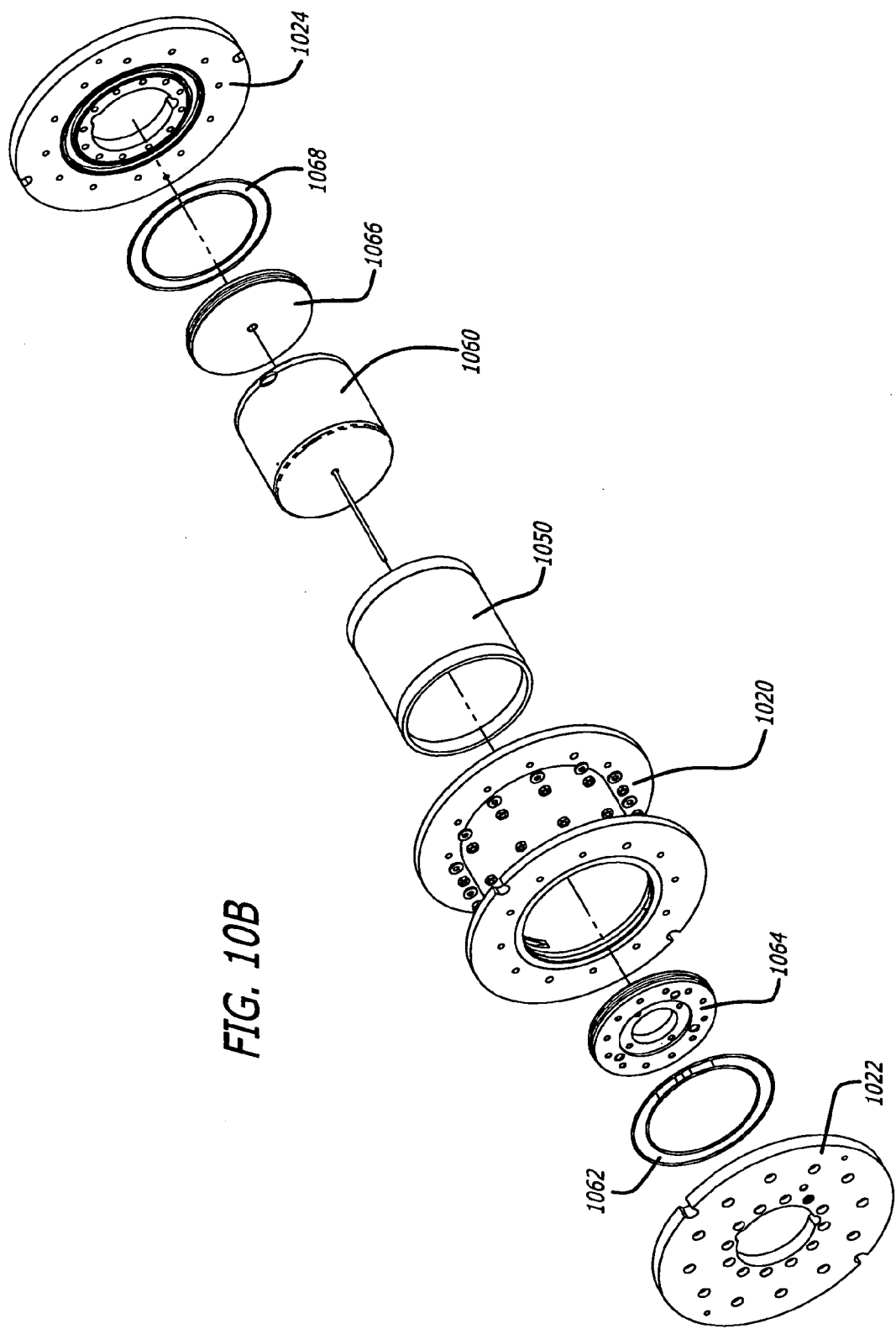

Referring now to FIGS. 10A and 10B, an alternative embodiment of the PRAL device 1000 may be further configured with a rotating core mechanism. The PRAL device includes an outer body 1020 having a lower portion 1022 and an upper portion 1024. A motor drive mechanism 1025 is configured within the lower portion. A gas inlet port 1040 is also configured in the lower portion of the housing. A stationary fiber bundle 1050 is positioned within the main body 1020 of the housing that is configured to accept a rotating cord 1060. Various seals and securing devices 1062, 1064, 1066 and 1068 are shown in FIG. 10B.

Figure 11:
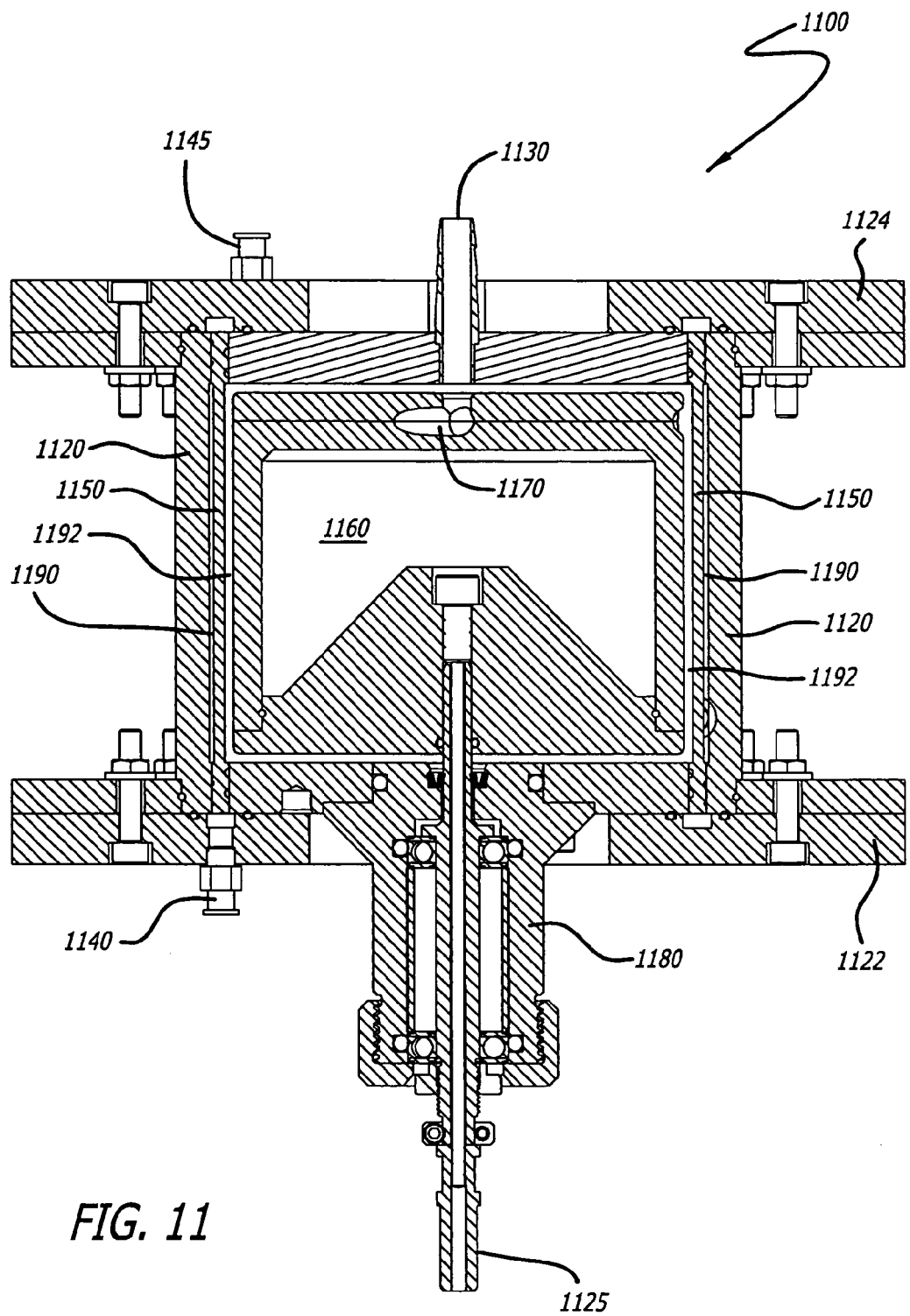
FIG. 11 is a cross-sectional view of the paracorporeal respiratory assist lung of FIG. 10.

Referring now to FIG. 11, the PRAL device 1100 is also configured with a rotating core mechanism and stationary fiber bundle. The device is configured with an outer housing 1120 having a lower portion 1122 and an upper portion 1124 that are secured together forming a single unit. The lower portion of the housing includes a motor drive mechanism 1125 operably secured to a rotating core 1160. Blood enters from a top portion of the unit through a blood entry port 1130 and travels to an impeller 1170. Blood flows from the impeller through an internal gap 1192 past the stationary fiber bundle 1150 through an outer recirculation gap 1190 and through an exit blood port (not shown). Gas enters the fiber bundle through an entry port 1140 and exits after passing through the fiber bundle through an exit port 1145 configured at the top of the PRAL device. The gas entry port is located in the lower portion 1122 of the PRAL housing 1120. A stabilizing portion 1180 secured to the lower portion of the housing includes bearings and seals configured to accept the rotating drive mechanism 1125. Other various seals and bearings may be employed to separate gas and blood flow and to prevent leakage of the fluids.

Figure 12A:
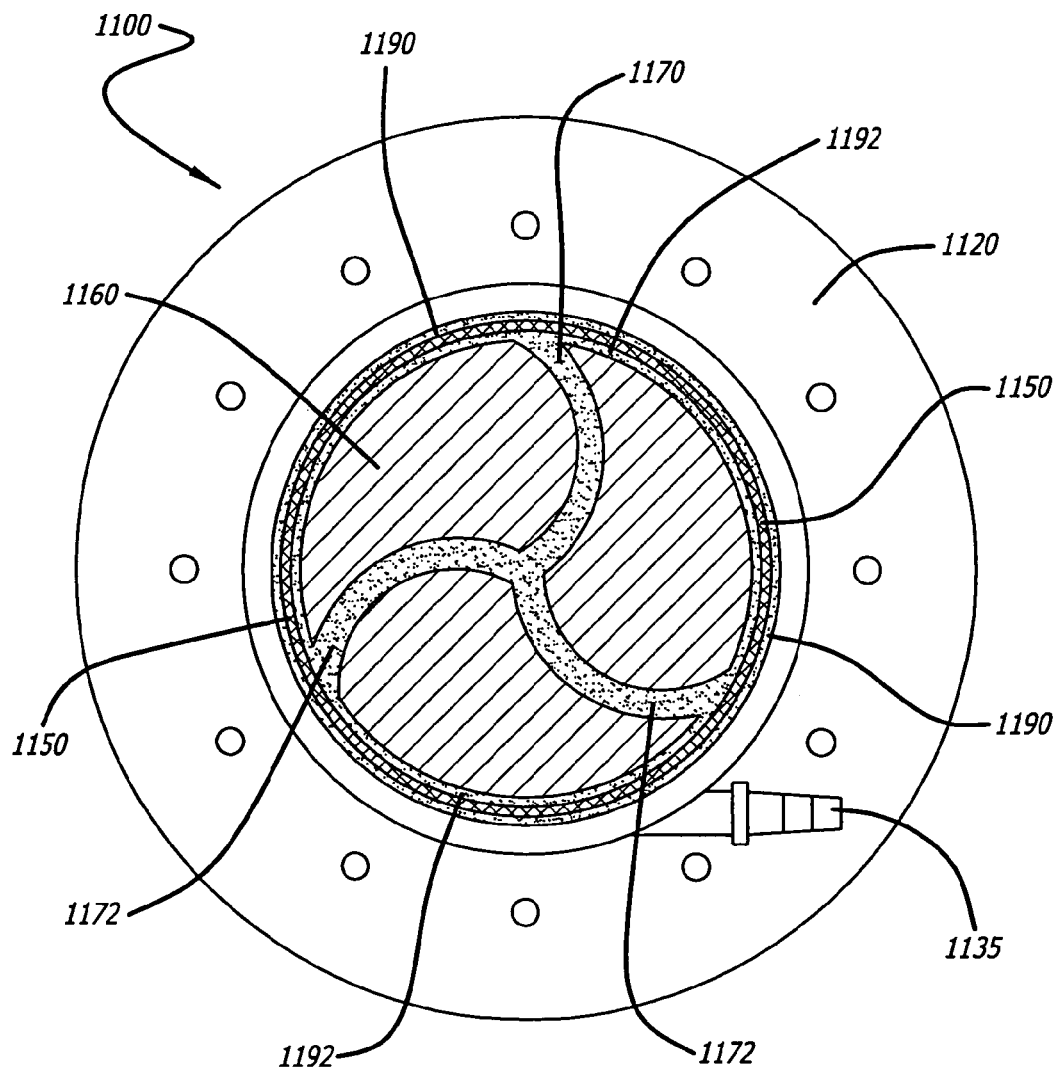
FIGS. 12A and 12B are schematic representations of the paracorporeal respiratory assist lung of FIG. 11.
Figure 12B:
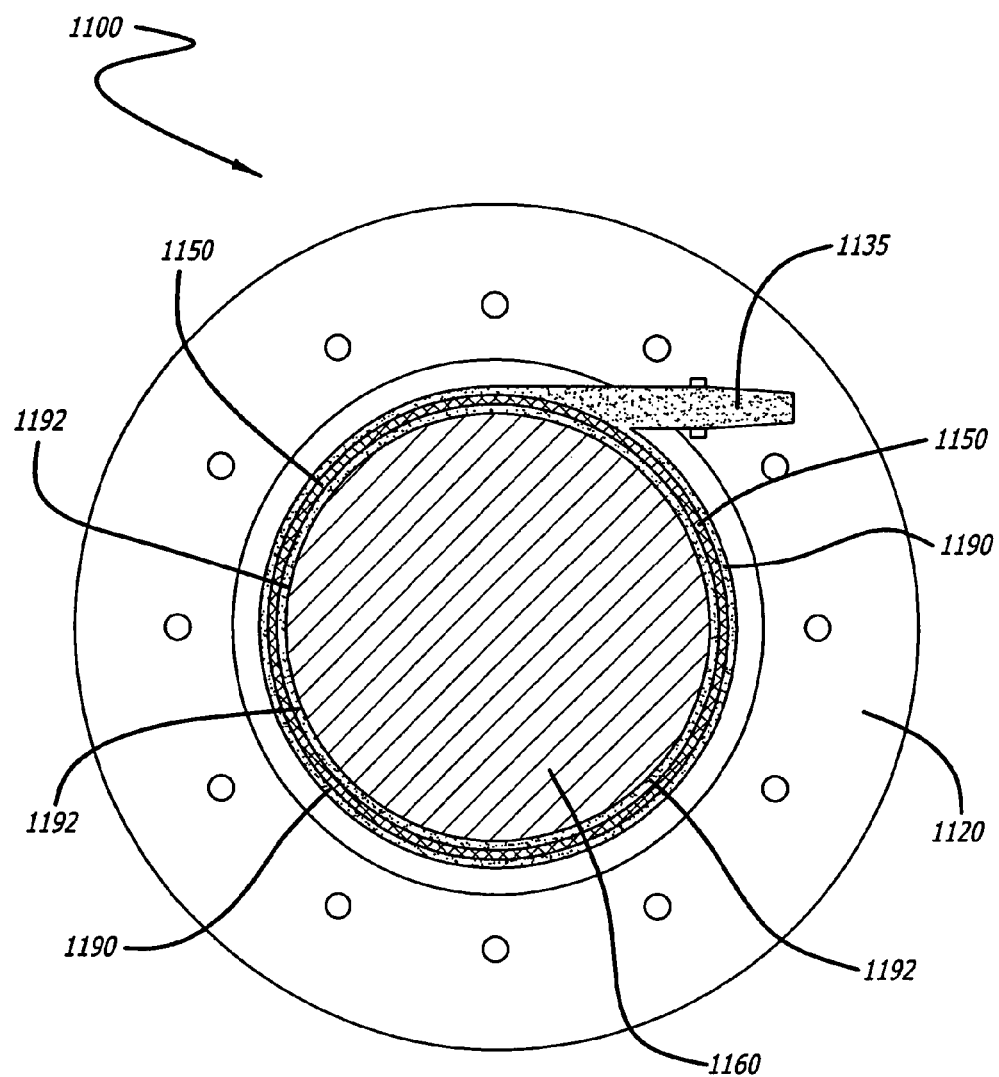

Referring now to FIGS. 12A and 12B, top and bottom views in partial cutaway are shown regarding the PRAL device of FIGS. 10 and 11. As shown in FIG. 12A, blood flow is directed into impeller 1170 having a plurality of arcuate flow directing arms 1172. The blood flow continues from the impeller to an internal gap 1192 disposed between the rotating core 1160 and stationary fiber bundle 1150. The blood flow travels through the stationary fiber bundle to an outer recirculation gap 1192 and out through the blood exit port 1135.

Figure 26:
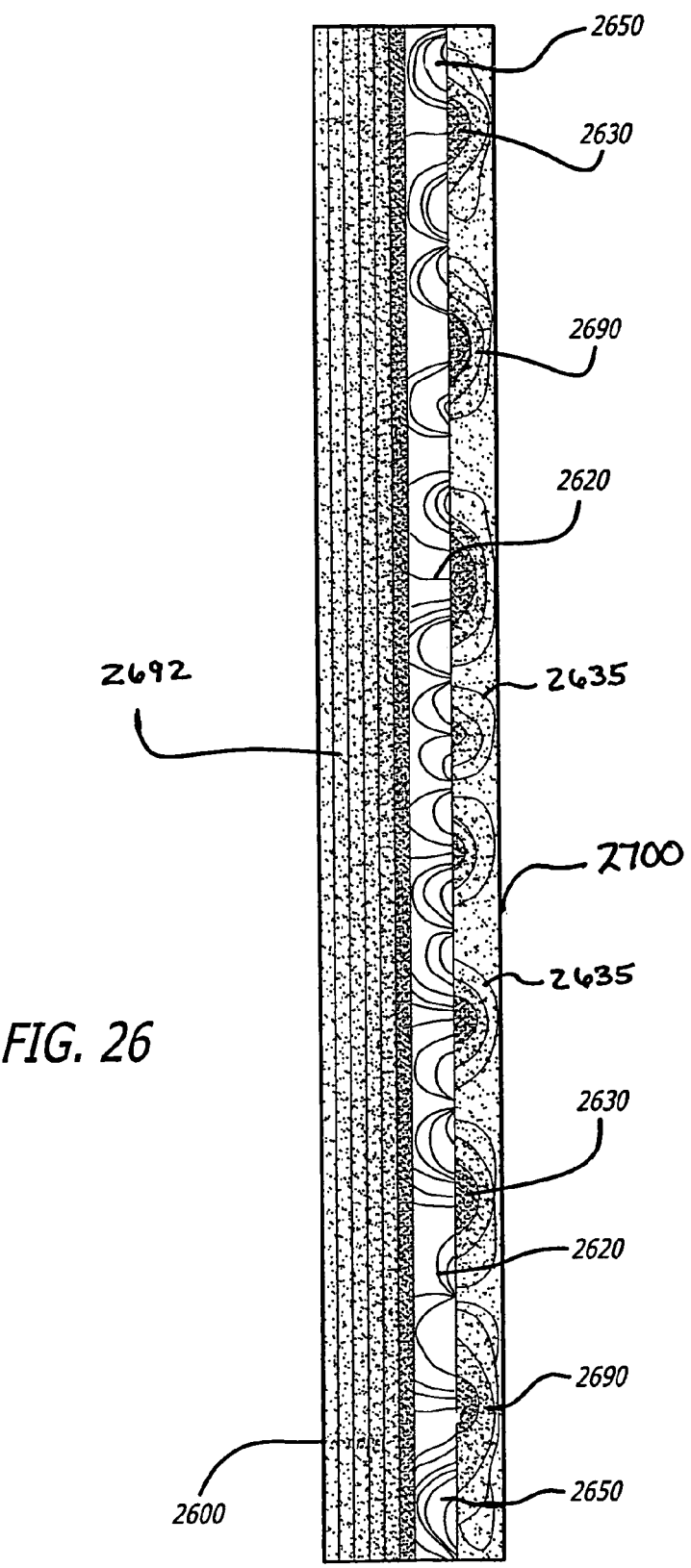
FIG. 26 is a graphical representation of the model (FEM-LAB) of blood flow through the fiber bundle.

FIG. 26 is a FEMLAB CFD (computational fluid dynamics) simulation of blood flow occurring in one embodiment of the PRAL device of the present invention. Shown is the longitudinal cross-section of the FEMLAB model for the case of a PRAL device with a rotating fiber bundle 2650 positioned between a stationary inner housing 2600 and a stationary outer housing 2700. A first outer gap 2690 is formed between the outer housing 2700 and the fiber bundle 2650, and a second inner gap 2692 is formed between the inner housing 2600 and the fiber bundle 2650. Rotation of the annular fiber bundle 2650 creates Taylor vortices 2635 in the outer gap 2690 between the rotating fiber bundle 2650 and the stationary outer housing 2700. The vortices 2635 create pressure variations 2630 in the outer gap 2690. The pressure variations disturb the blood flow pattern 2620 within the fiber bundle 2650, augmenting relative velocity between the rotating fibers and the blood, thereby improving gas exchange. In this and other embodiments of the PRAL device, the size of the outer gap 2690 between the annular fiber bundle 2650 (rotating or stationary) and the outer housing 2700 has a preferred size range. The gap size should be just large enough that the pressure drop encountered by blood traversing the outer gap 2690 to the device outlet be configured so as to not prevent the establishment of a relatively uniform distribution of radial blood flow through the annular fiber bundle 2650. This gap size will be conditional on the permeability (porosity) and thickness of the fiber bundle.

Figure 13:
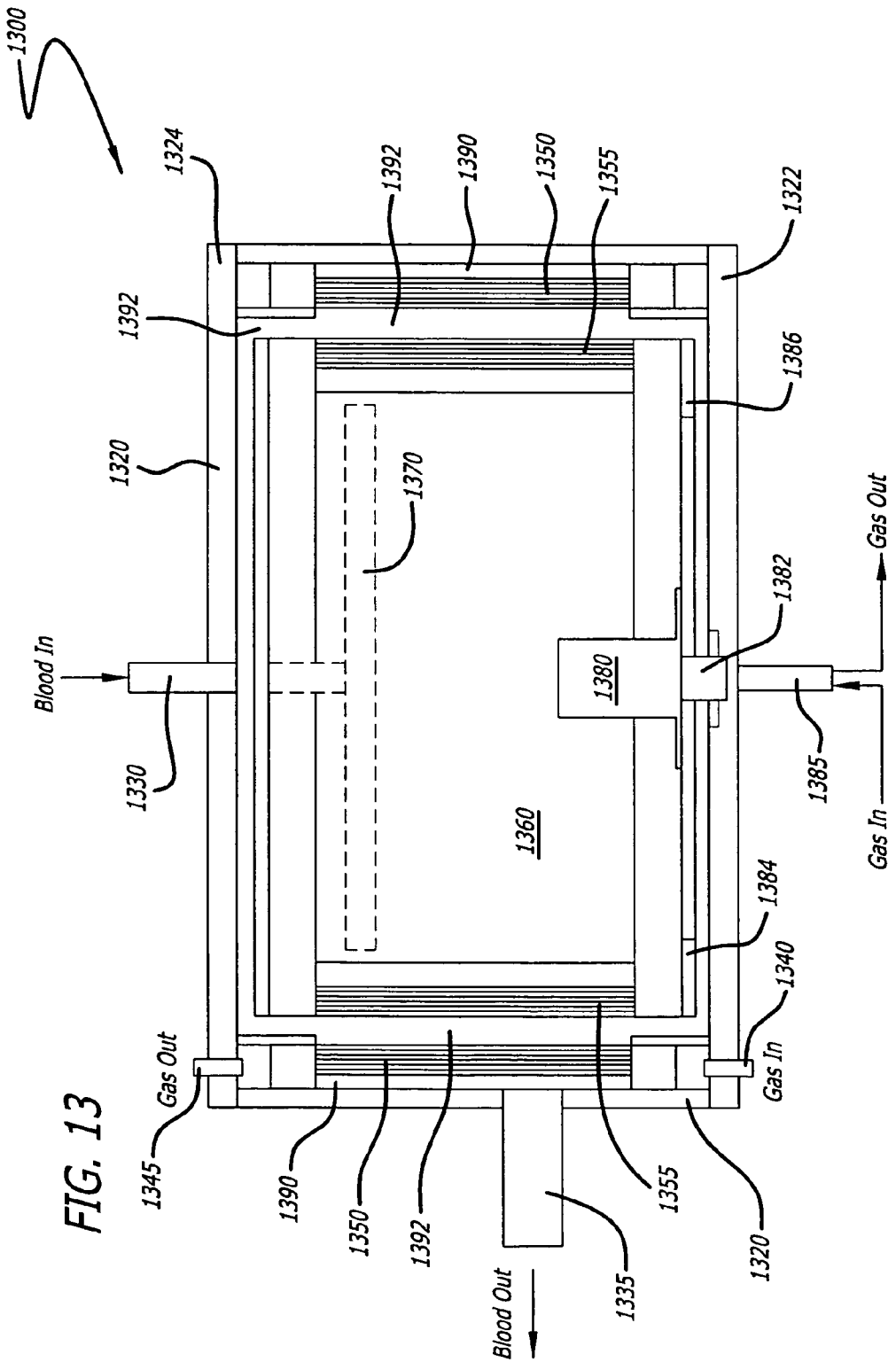
FIG. 13 depicts schematic view of an alternative embodiment of the paracorporeal respiratory assist lung of the present invention.

Referring now to FIG. 13, an alternative embodiment of the PRAL device of the present invention includes a bundle of fibers configured with the rotating core in addition to a stationary fiber bundle. The PRAL device includes a housing 1320 having a lower portion 1322 and an upper portion 1324. The upper portion includes a blood inlet conduit 1330 that is connected to a blood distribution impeller 1370 embodied within the rotating core 1360. The lower portion of the body 1322 includes seals and bearings 1380 and a pin or other mechanism 1382 for the rotating core to rest within the housing. This embodiment of the PRAL device includes a stationary fiber bundle 1350 having a gas inlet 1340 and a gas outlet 1345. Blood flows from the inlet 1330 through an internal gap 1322 past the bundles 1350 through a recirculation gap 1390 and out the blood exit port 1335. The internal and recirculation gaps between the rotating core and the outer housing allow for a recirculation or eddy effect. The rotating core is magnetically coupled to an external device via magnets 1384 and 1386 secured to the rotating core. Additional conduit 1385 is included for providing gas flow into and out of the rotating fiber bundle 1355.

Figure 14:
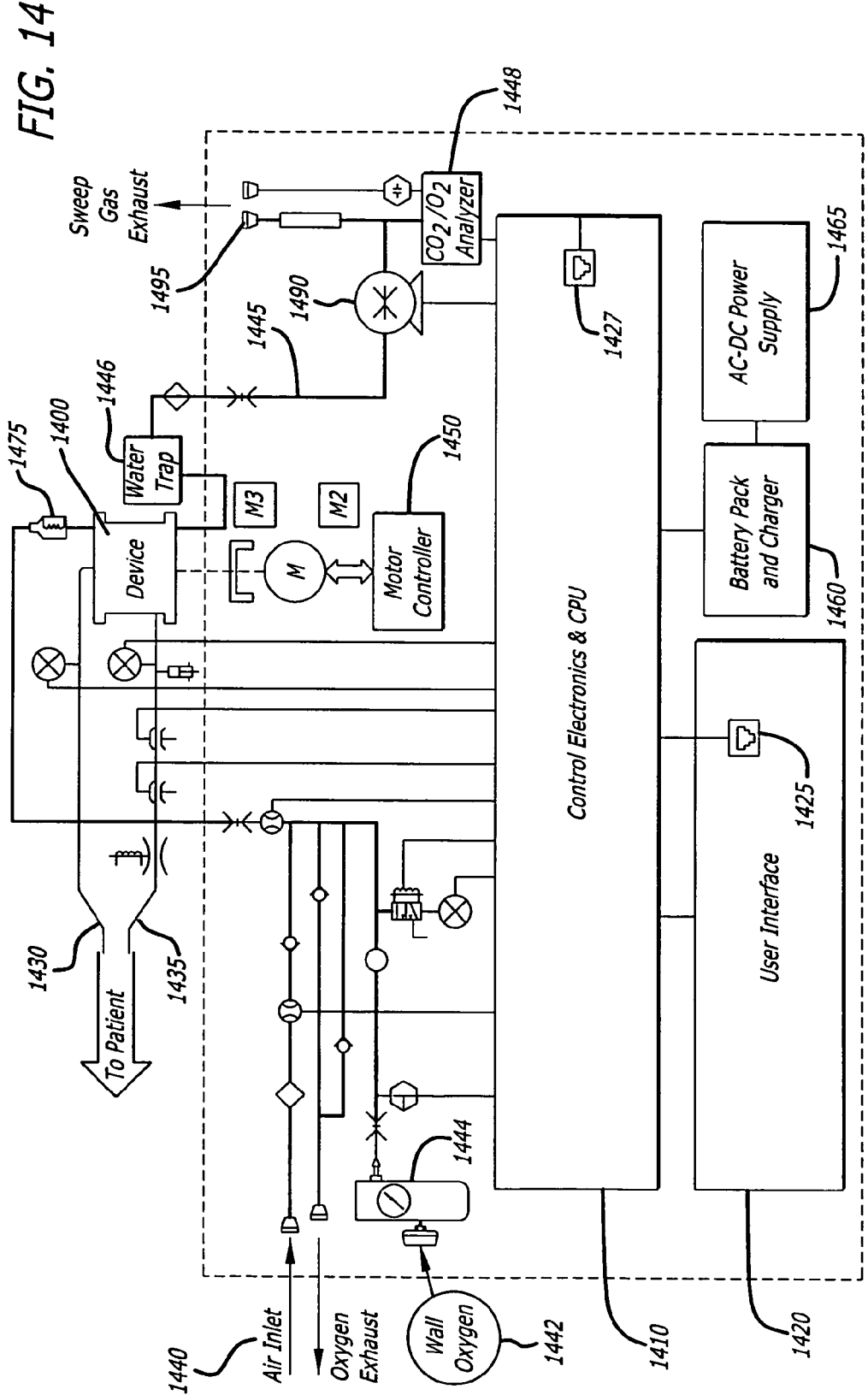
FIG. 14 is a block diagram of the system of the present invention.

Referring now to FIG. 14, a block diagram is shown depicting the PRAL device 1400 configured with control in electronics computer system 1410 having a user interface 1420 with battery pack and charger 1430 and AC-DC power supply 1435. The system may be further configured with Ethernet or other external communication devices 1425, 1427. Blood enters the PRAL device through inlet line 1430 and exits to the patient through outlet port 1435 having safety mechanisms such as flow and bubble detectors. An air inlet 1440 is supplied and may be connected to a wall oxygen supply unit 1442 or oxygen tank 1444 for supplementing gas to the device. A humidifier and/or heater 1475 may be interposed between the air inlet and the PRAL device 1400. The sweep gas exhaust line 1445 may include a water trap 1446 and carbon dioxide and oxygen analyzers 1448. Other valves and venting mechanisms may be included for safety devices. For example, a vacuum pump 1490 may be interposed between the PRAL device 1400 and the exit ports 1495 to create a safety mechanism so that the system has a negative pressure so as to not create bubbles within the patient's vasculature.

Figure 15:
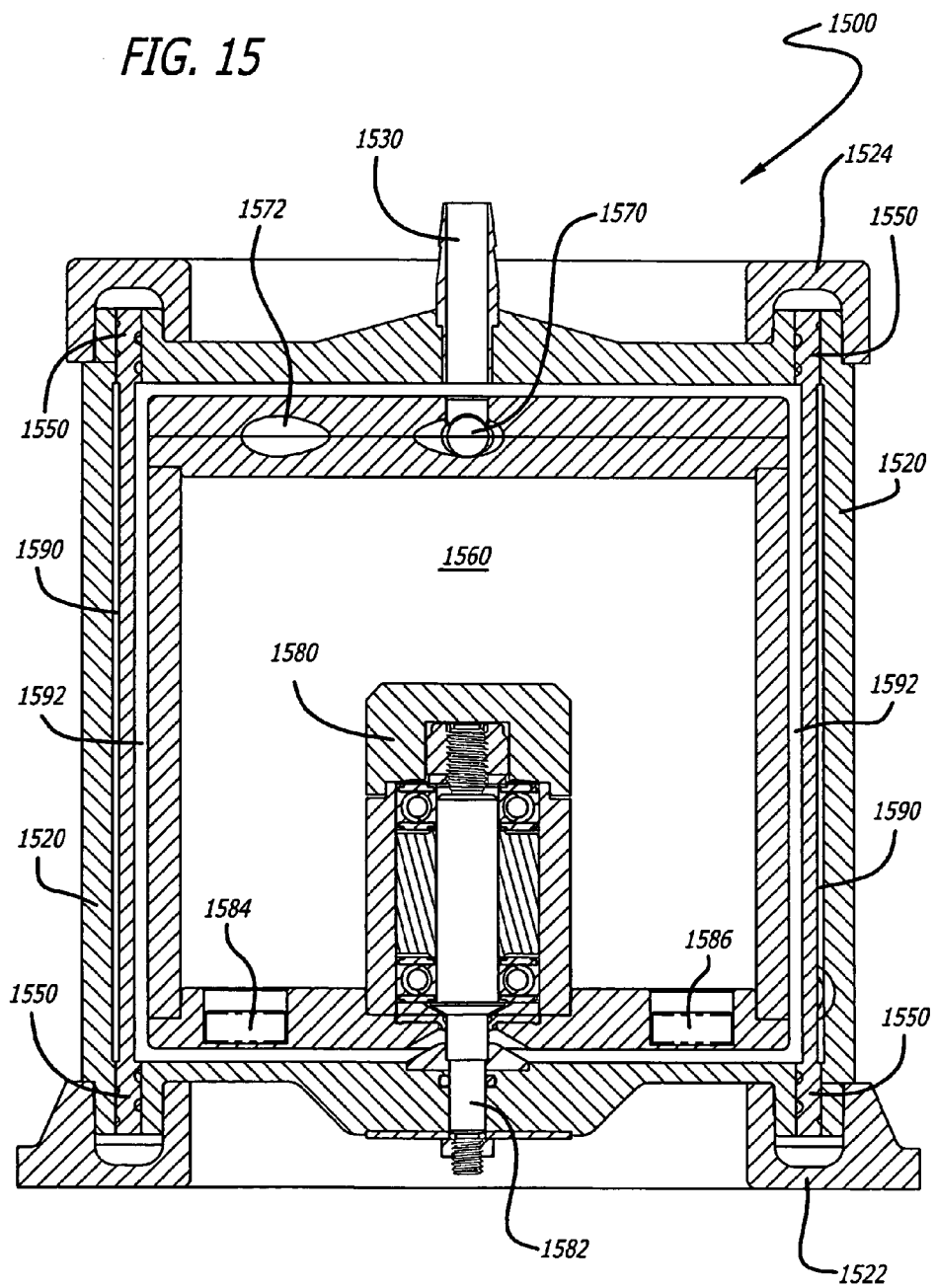
FIG. 15 depicts a cross-sectional view of an alternative embodiment of the paracorporeal respiratory assist lung of the present invention having a magnetic drive mechanism.

FIG. 15 depicts an alternative embodiment of the PRAL device of the present invention. The PRAL device 1500 is also configured with a rotating core mechanism and stationary fiber bundle. The device is configured with an outer housing 1520 having a lower portion 1522 and an upper portion 1524 that are secured together forming a single unit. The lower portion of the housing includes a drive mechanism 1580, 1582 operably secured to a rotating core 1560. Blood enters from a top portion of the unit through a blood entry port 1530 and travels to an impeller 1570 having a plurality of arms 1572. Blood flows from the impeller through an internal gap 1592 past the stationary fiber bundle 1550 through an outer recirculation gap 1590 and through an exit blood port (not shown). Gas enters the fiber bundle through an entry port (not shown) and exits after passing through the fiber bundle through an exit port (not shown) configured at the top of the PRAL device. The gas entry port is located in the lower portion 1122 of the PRAL housing 1120. The device includes magnets 1584 and 1586 for coupling to an external drive mechanism. Other various seals and bearings may be employed to separate gas and blood flow and to prevent leakage of the fluids. The magnets and housing may be configured to allow the rotating core to levitate above the bottom portion of the housing, thereby reducing friction in the device. Other various seals and bearings may be employed to separate gas and blood flow and to prevent leakage of the fluids.

While particular forms of the invention have been illustrated and described, it will also be apparent to those skilled in the art that various modifications can be made without departing from the inventive concept. References to use of the invention with a membrane electrode assembly and fuel cell are by way of example only, and the described embodiments are to be considered in all respects only as illustrative and not restrictive. The present invention may be embodied in other specific forms without departing from its spirit or essential characteristics. Accordingly, it is not intended that the invention be limited except by the appended claims.

We claim:

1. A paracorporeal respiratory assist lung, comprising:
    a housing having a smooth inner cylindrical surface, a liquid inlet, a liquid outlet, a gas inlet and a gas outlet;
    a plurality of tubular gas permeable fiber membranes configured to form a cylindrical annular fiber bundle, the annular fiber bundle being disposed within the housing and connected to and in fluid communication with the gas inlet and the gas outlet wherein gas is passed through the lumens of the cylindrical annular fiber bundle, wherein a first annular gap is configured between the housing and the fiber bundle;
    a stationary cylindrical core with a smooth outer surface being positioned concentrically within the annular fiber bundle, wherein a second annular gap is configured between the smooth outer surface the core and the annular fiber bundle; a stationary cylindrical core with a smooth outer surface being positioned concentrically within the annular fiber bundle, wherein a second annular gap is configured between the smooth outer surface of the core and the fibers of the annular fiber bundle; an impeller having the same diameter as the core and in fluid communication with the liquid inlet via a conduit within the core, the impeller fixed to the interior of a lower portion of the annular fiber bundle; the impeller comprised of a plurality of arcuate arms each culminating in an exit port aligned with the smooth outer surface of the stationary core and ending in the lower portion of the second annular gap; and
    means for rotating the annular fiber bundle and fixed impeller, wherein rotating the annular fiber bundle cooperates with the smooth inner surface of the housing and the first annular gap to create and maximize Taylor vortices within the first annular gap; and
    wherein the housing, annular fiber bundle and core are configured such that liquid traveling at a low flow rate enters the liquid inlet, travels down the conduit through the impeller which pumps the liquid in to the second annular gap and radially through the tubular gas permeable hollow fiber membrane, having the Taylor vortices cause the liquid to pass the back and forth through the fiber bundle and the annular gaps to maximize gas exchange, the liquid eventually exiting through the liquid outlet.

2. The paracorporeal respiratory assist lung of claim 1, wherein the fiber bundle is configured with a porosity that allows uniform liquid flow though the fiber bundle; said porosity is determined by the diameter of the hollow fiber membrane and by arrangement and spacing between hollow fiber membranes.

3. The paracorporeal respiratory assist lung of claim 1, further comprising means for varying a velocity of the rotation of the fiber bundle.

4. The paracorporeal respiratory assist lung of claim 1, further comprising means for oscillating a direction of the rotation of the fiber bundle.

5. The paracorporeal respiratory assist lung of claim 1, further comprising a dual lumen cannula configured for insertion into the venous circulation of a patient to provide blood flow to the liquid inlet of the housing and to accept blood flow from the liquid outlet of the housing.

* * * * *